US012674162B2

(12) United States Patent
Grainok et al.

(10) Patent No.: US 12,674,162 B2
(45) Date of Patent: Jul. 7, 2026

(54) COMPOSITIONS AND METHODS FOR TREATMENT OF KIDNEY DISEASE

(71) Applicant: PYC THERAPEUTICS LIMITED, Nedlands (AU)

(72) Inventors: Janya Grainok, Nedlands (AU); Anja Stirnweiss, Nedlands (AU)

(73) Assignee: PYC THERAPEUTICS LIMITED, Nedlands (AU)

( * ) Notice: Subject to any disclaimer, the term of this patent is extended or adjusted under 35 U.S.C. 154(b) by 0 days.

(21) Appl. No.: 19/219,917

(22) Filed: May 27, 2025

(65) Prior Publication Data

US 2025/0283086 A1     Sep. 11, 2025

Related U.S. Application Data

(63) Continuation of application No. PCT/AU2024/050616, filed on Jun. 13, 2024.

(30) Foreign Application Priority Data

Jun. 16, 2023   (AU) ................................ 2023901907
Sep. 21, 2023   (AU) ................................ 2023903042

(51) Int. Cl.
     *C12N 15/113*        (2010.01)
     *A61P 13/12*         (2006.01)
(52) U.S. Cl.
     CPC ............ *C12N 15/113* (2013.01); *A61P 13/12* (2018.01); *C12N 2310/11* (2013.01); *C12N 2310/3233* (2013.01); *C12N 2310/3513* (2013.01)
(58) Field of Classification Search
     None
     See application file for complete search history.

(56) References Cited

FOREIGN PATENT DOCUMENTS

| | | | | |
|---|---|---|---|---|
| WO | 2017/035319 A1 | 3/2017 | | |
| WO | 2017/106211 A1 | 6/2017 | | |
| WO | 2018/106566 A1 | 6/2018 | | |
| WO | 2018/106568 A1 | 6/2018 | | |
| WO | 2021/119756 A1 | 6/2021 | | |
| WO | 2023/060237 A1 | 4/2023 | | |
| WO | WO-2024178336 A2 * | 8/2024 | ........... | C12N 15/113 |
| WO | 2024/215846 A1 | 10/2024 | | |
| WO | WO-2024259175 A2 * | 12/2024 | ........... | C12N 15/113 |
| WO | 2025/165891 A1 | 8/2025 | | |
| WO | 2025/193584 A1 | 9/2025 | | |

OTHER PUBLICATIONS

Wang (2011. The Principles of MiRNA-Masking Antisense Oligonucleotides Technology. Ch. 3 in MicroRNA and Cancer: Methods and Protocols, Methods in Molecular Biology, vol. 676, Springer) (Year: 2011).*

Cornec Le Gall (et al. 2013. Type of PKD1 Mutation Influences Renal Outcome in ADPKD. J. Am. Soc. Nephrol. 24[6]:1006-1013) (Year: 2013).*

Lima (et al. 2018. Anti-miRNA oligonucleotides: A comprehensive guide for design. RNA Biol. 3:338-352) (Year: 2018).*

Abdulbagi (et al. 2021. D-Amino Acids and D-Amino Acid-Containing Peptides: Potential Disease Biomarkers and Therapeutic Targets? Biomolecules 11[11]:1716) (Year: 2021).*

Gu (et al. 2025. Advances and Challenges in Modeling Autosomal Dominant Polycystic Kidney Disease: A Focus on Kidney Organoids. Biomedicines 13[2]:523) (Year: 2025).*

Hopp (et al. 2012. Functional polycystin-1 dosage governs autosomal dominant polycystic kidney disease severity. J. Clin. Invest 122[11]:4257-4273) (Year: 2012).*

Ramalingham et al., "Modulation of polycystic kidney disease by non-coding RNAs," Cellular Signalling, 71, 33 pp. (2020).

Lakhia et al., "PKD1 and PKD2 mRNA cis-inhibition drives polycystic kidney disease progression," Nature Communications, 13:4765, 14 pp. (Aug. 15, 2022).

Australian Patent Office, International Search Report in International Patent Application No. PCT/AU2024/050616, 8 pp. (Jul. 30, 2024).

Australian Patent Office, Written Opinion in International Patent Application No. PCT/AU2024/050616, 5 pp. (Jul. 30, 2024).

De Carvalho Ribeiro et al., "Differentiating Induced Pluripotent Stem Cells into Renal Cells: A New Approach to Treat Kidney Diseases," Stem Cells International, 2020, 8894590, 9 pp. (Aug. 7, 2020).

Dugal-Tessier et al., "Antibody-Oligonucleotide Conjugates: A Twist to Antibody-Drug Conjugates," Journal of Clinical Medicine, 10 (838), 17 pp. (Feb. 18, 2021).

Osafune, "iPSC technology-based regenerative medicine for kidney diseases," Clinical and Experimental Nephrology, 25, 574-584 (Mar. 3, 2021).

Prakash et al., "Fatty acid conjugation enhances potency of antisense oligonucleotides in muscle," Nucleic Acids Research, 47 (12), 6029-6044 (May 25, 2019).

Sharma et al., "In vitro cyst formation of ADPKD cells," Methods in Cell Biology, 153, 93-111 (2019).

PYC's Fourth Drug Candidate has Disease-Modifying Potential in Polycystic Kidney Disease. ASX announcement. 5 pp. (Nov. 13, 2023).

Supplementary Information. ASX announcement. 7pp. (Nov. 16, 2023).

Polycystic Kidney Disease Drug Candidate Progressing to Human Trials. ASX announcement, 5 pp. (Apr. 22, 2024).

PYC to Progress Kidney Drug Candidate into Human Trials. ASX announcement, 34 pp. (Nov. 27, 2024).

(Continued)

*Primary Examiner* — Nancy J Leith
*Assistant Examiner* — Ruth Sophia Arieti
(74) *Attorney, Agent, or Firm* — Morgan, Lewis & Bockius LLP

(57)     ABSTRACT

Described herein are antisense oligonucleotides, vectors, and related compositions and methods for increasing expression of PKD1 mRNA and Polycystin 1 protein and uses thereof for the treatment of autosomal dominant polycystic kidney disease (ADPKD).

10 Claims, 12 Drawing Sheets

Figure 1:
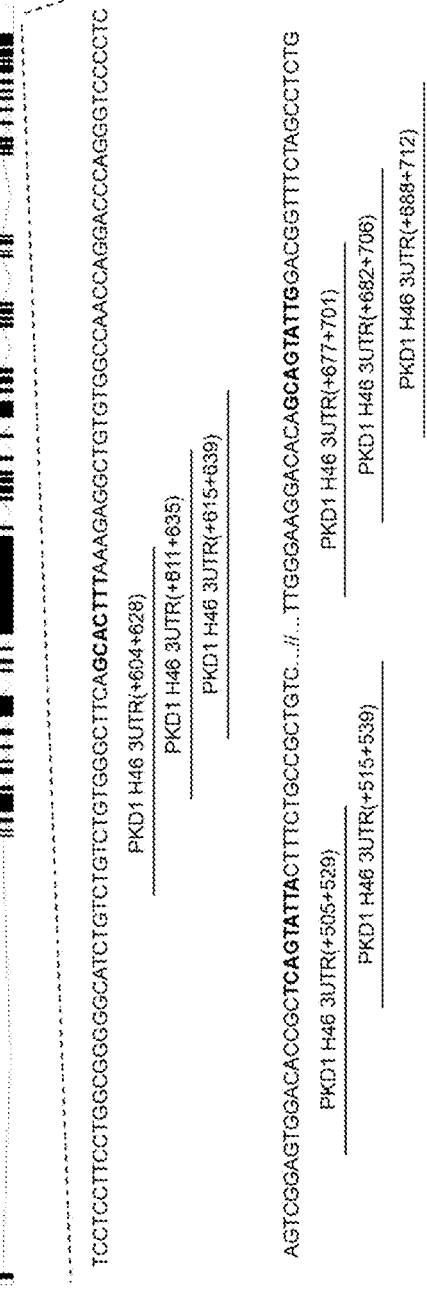

Specification includes a Sequence Listing.

(56)            References Cited

OTHER PUBLICATIONS

Polycystic Kidney Disease Program Investor Presentation. ASX announcement presentation, 12 pp. (Nov. 28, 2024).

Patel et al., "miR-17~92 miRNA cluster promotes kidney cyst growth in polycystic kidney disease," PNAS, 110 (26), 10765-10770 (Jun. 25, 2013).

Badal et al., "MicroRNAs and Their Applications in Kidney Diseases," Pediatr Nephrol, 30 (5), 727-740 (May 2015).

Hajarnis et al., "microRNA-17 family promotes polycystic kidney disease progression through modulation of mitochondrial metabolism," Nature Communications, 8, 14395, 15 pp. (Feb. 16, 2017).

Lee et al., "Discovery and preclinical evaluation of anti-miR-17 oligonucleotide RGLS4326 for the treatment of polycystic kidney disease," Nature Communications, 10, 4148, 14 pp. (2019).

Regulus Therapeutics Reports Third Quarter 2021 Financial Results and Recent Updates Exhibit 99.1, 5 pp. (2021).

Lee et al., Poster Abstract: Discovery of anti-miR-17 oligonucleotide RGLS4326 for the treatment of autosomal dominant polycystic kidney disease, 2 pp. (2022).

Drygin, "Lessons Learned from Preclinical and Clinical Development of microRNA Therapies," RNA Leaders World Congress, Basel, 24 pp. (Mar. 17, 2022).

Patel, "PKD1 derepression as a potential therapy for Polycystic Kidney Disease," NIH Proj. No. 5R01DK133186-04, 6 pp. (2025).

Edmund et al., "Discovery of Next-Generation Anti-miR-17 Oligonucleotide RGLS8429 for Treatment of Autosomal Dominant Polycystic Kidney Disease (ADPKD)," American Society of Nephrology, Abstract: TH-PO408, 2 pp. (2022).

* cited by examiner

A
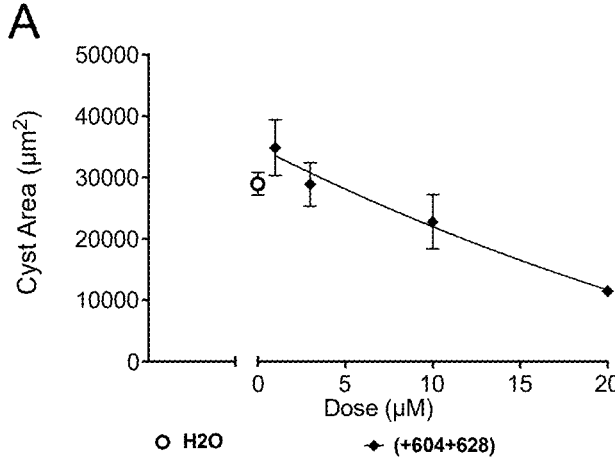
B
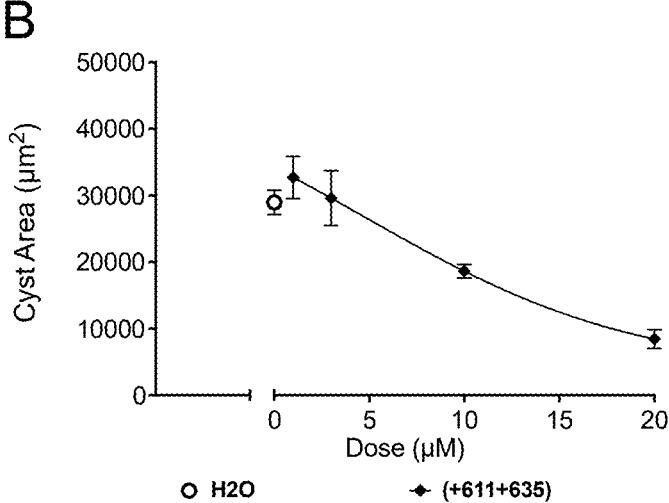
FIGURE 5(A-B)

C
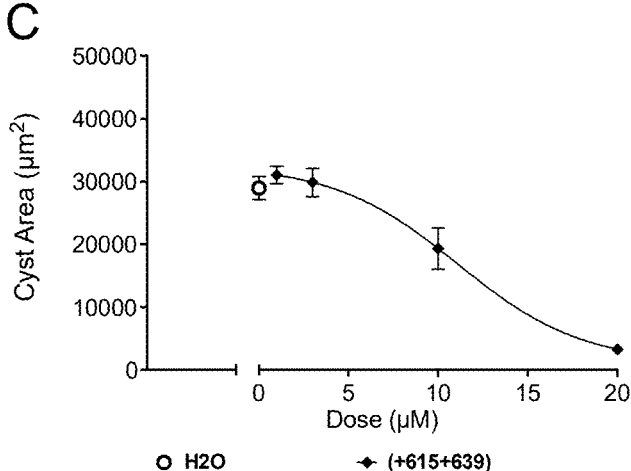
D
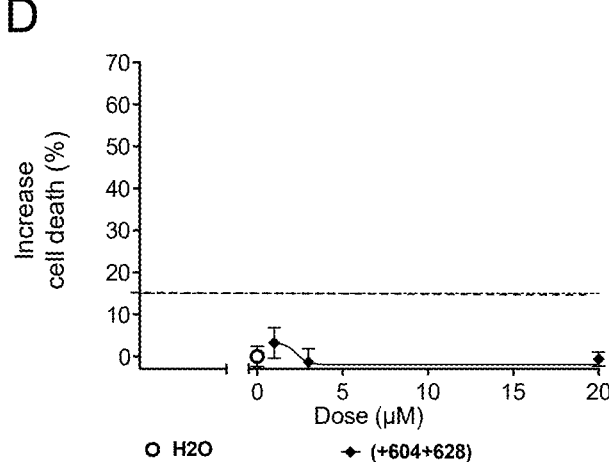
FIGURE 5(C-D)

E
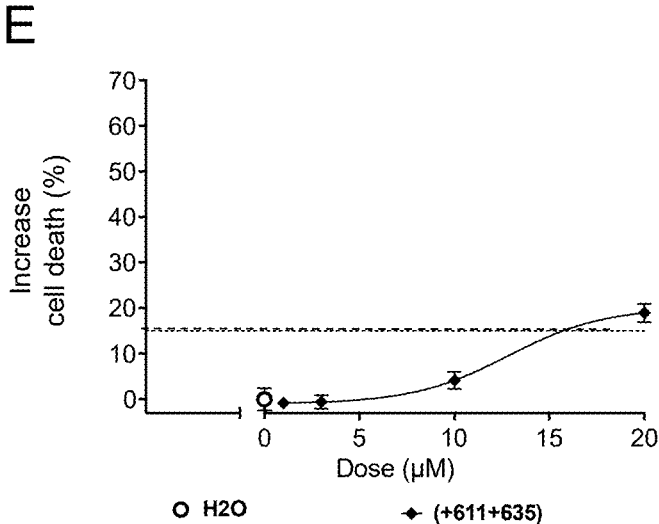
F
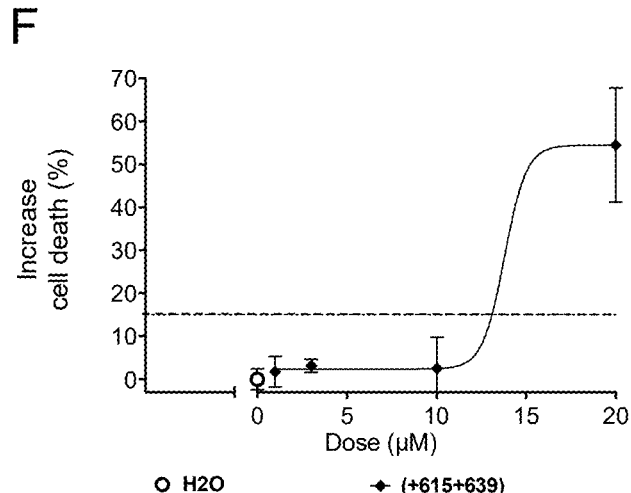
FIGURE 5(E-F)

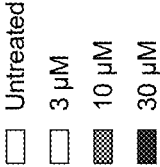
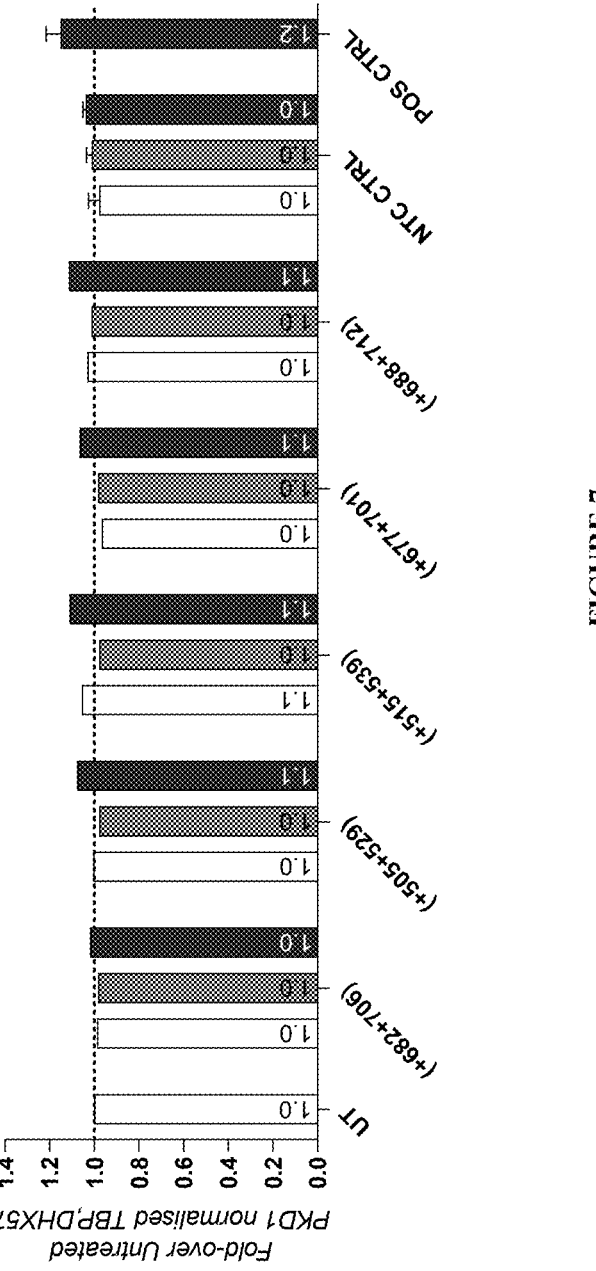
FIGURE 7

COMPOSITIONS AND METHODS FOR TREATMENT OF KIDNEY DISEASE

CROSS-REFERENCE TO RELATED APPLICATIONS

The present application is a continuation application of International Patent Application No. PCT/AU2024/050616 filed on 13 Jun. 2024, which claims priority from AU 2023901907 filed on 16 Jun. 2023, and AU 2023903042 filed on 21 Sep. 2023, the entire contents of each of which are incorporated herein by reference.

SEQUENCE LISTING

The instant application contains a Sequence Listing which has been submitted electronically in XML format and is hereby incorporated by reference in its entirety. Said XML copy, created on May 27, 2025, is named "047763-5025-US Sequence Listing.xml" and is approximately 461,704 bytes in size.

TECHNICAL FIELD

The present disclosure generally is directed to oligonucleotides and related compositions and methods for treating conditions associated with mutations in the Polycystic Kidney Disease 1 (PKD1) gene.

BACKGROUND

Autosomal dominant polycystic kidney disease (ADPKD) is the most common inherited nephropathy that leads to end-stage renal disease (ESRD). Approximately 1 in 500-2,500 individuals carry a mutation for this condition. ADPKD is a progressive disorder that is characterised by an abnormal expansion of renal tubule cells resulting in the growth of multiple cysts in the kidney.

Cyst development starts early in life and in the more severe cases in utero and is commonly followed by a prolonged period of asymptomatic progression. Signs and symptoms of ADPKD usually present between the ages of 30 and 40. However, approximately 3% of ADPKD patients have either very-early-onset or unusually rapid progressive disease. Consistent with the decline in renal function patients present with various urinary complications such as cyst and urinary tract infections, a decline in glomerular filtration rate, chronic lower back pain and hypertension. ADPKD patients often present with additional extra-renal conditions including hepatic cysts (in >90% of patients aged >35 years), pancreatic cysts, intracranial aneurysms, colon diverticulosis, and heart valve defects. Overall, ADPKD is associated with significant morbidity a reduced life expectancy.

ADPKD is predominantly caused by a mutation in one of the polycystin genes; PKD1(Poly cystin 1, Transient Receptor Potential Channel Interacting) (74-85% of patients) or PKD2 (15-26%). The phenotype of patients with a PKD1mutation is usually more severe compared to those with PKD2 mutations, which is reflected in approximately 20 years difference in the mean age of ESRD (54.3 years in PKD1 vs 74.0 years in PKD2 disease).

There is an ongoing need to provide new treatments or preventative measures for ADPKD.

SUMMARY

PKD1 consists of 46 exons spanning approximately 50 kb of genomic DNA on the short arm of chromosome 16

(16p13.3). The canonical PKD1-encoded Polycystin 1 protein is a 4,303 amino acid, glycosylated integral membrane protein that localises to primary cilia, endoplasmic reticulum, adherent and desmosomal junctions, apical membranes, plasma membrane and junctional complexes. Polycystin 1 contains a large N-terminal extracellular region, multiple transmembrane domains, and a cytoplasmic C-tail and functions as a regulator of calcium-permeable cation channels and intracellular calcium homoeostasis. It is also involved in cell-cell/matrix interactions and modulation of G-protein-coupled signal-transduction pathways. Splice variants encoding different isoforms have been noted for this gene.

While not wishing to be bound by theory, it is believed that kidney cysts develop in ADPKD once the level of Polycystin 1 function falls below a specific level. Indeed, this is consistent with the fact that the level of residual Polycystin 1 function from the mutated gene directly correlates with disease severity. The median age at onset of ESRD was 55 years for carriers of a truncating mutation (complete loss of function) and 67 years for carriers of a non-truncating mutation (partial loss of function).

The present disclosure provides antisense oligonucleotides (ASO), antisense RNA (AR) expression vectors, and related compositions and methods to increase PKD1 mRNA and/or Polycystin 1 protein levels by modulating the post-transcriptional or translational regulation of the 3' untranslated region (UTR) of PKD1 mRNA, e.g., by blocking specific binding of mirR-17 family miRNAs (e.g., miR-17-5p, miR-106a-5p, miR-106b-5p, miR-20a-5p, miR-93-5p) or miR-200 family miRNAs (e.g., miR-200b, miR200c, or miR-429) to their cognate binding sites.

Accordingly, in one aspect provided herein is an ASO that binds to a targeted portion of the 3' UTR of a PKD1 mRNA, wherein binding of the antisense oligonucleotide to the targeted portion increases the level of Polycystin 1 protein. In another aspect provided herein is an ASO that binds to a targeted portion of the 3' untranslated region (UTR) of a Polycystic Kidney Disease 1 (PKD1) mRNA, wherein binding of the antisense oligonucleotide to the targeted portion reduces kidney cyst growth or size when introduced into a 3D kidney cyst culture. In some examples binding of the antisense oligonucleotide to the targeted portion reduces specific binding of miR-17 family miRNAs (e.g., miR-17-5p, miR-106a-5p, miR-106b-5p, miR-20a-5p, miR-93-5p) or miR-200 family miRNAs (e.g., miR-200b, miR200c, or miR-429) to the 3' UTR. In some examples, where binding of the antisense oligonucleotide to the targeted portion reduces specific binding of mirR-17 family miRNAs (e.g., miR-17-5p, miR-106a-5p, miR-106b-5p, miR-20a-5p, miR-93-5p) or miR-200 family miRNAs (e.g., miR-200b, miR200c, or miR-429) to the 3' UTR, the antisense oligonucleotide comprises the sequence of any one of SEQ ID NOs:2-351 or 353-362.

In a further aspect provided herein is a vector for expression, in a mammalian cell, of an AR that binds to a targeted portion of the 3' UTR of a PKD1 mRNA, wherein binding of the AR to the targeted portion increases the level of Polycystin protein. In another aspect provided herein is a vector for expression, in a mammalian cell, of an AR that binds to a targeted portion of the 3' UTR of a PKD1 mRNA, wherein binding of the AR to the targeted portion reduces cyst growth when introduced into a 3D kidney cyst culture. In some examples binding of the AR to the targeted portion reduces specific binding of mirR-17 family miRNAs (e.g., miR-17-5p, miR-106a-5p, miR-106b-5p, miR-20a-5p, miR-93-5p) or miR-200 family miRNAs (e.g., miR-200b, miR200c, or miR-429) to the 3' UTR. In some examples, where binding of the AR to the targeted portion reduces specific binding of mirR-17 family miRNAs (e.g., miR-17-5p, miR-106a-5p, miR-106b-5p, miR-20a-5p, miR-93-5p) or miR-200 family miRNAs (e.g., miR-200b, miR200c, or miR-429) to the 3' UTR, the AR comprises or consists of the sequence of any one of any one of SEQ ID NOs:2-351 or 353-362. In some examples the vector is a non-viral vector. In other examples the vector is a viral vector. In some examples, where the vector is a viral vector, the viral vector is provided in a recombinant virus selected from the group consisting of: adeno-associated virus (AAV), adenovirus, lentivirus, and anellovirus.

In some examples the AR can be delivered by a vector (e.g., a plasmid or a recombinant virus) that comprises a kidney cell type-selective or tissue-selective promoter for driving expression of the AR in the mammalian cell. In some examples, the promoter is selective for expression in kidney cells selected from the group consisting of: pericytes, podocytes, parietal epithelial cells, proximal tubule cells, ascending loop of Henle cells, descending loop of Henle cells, distal tubule cells, connecting tubule cells, intercalated cells, principal cells, peritubular capillary endothelium cells, and glomerular endothelium cells. In some examples the vector includes an inducible promoter.

In some examples, in any of the foregoing ASOs or vectors, the ASO or the AR binds within a targeted portion of the 3' UTR corresponding to SEQ ID NO:1. In some examples the nucleotide sequence of the ASO or AR is at least 60%, 65%, 70%, 75%, 80%, 85%, 90%, 95%, or 100% complementary to the nucleotide sequence of the targeted portion over the length of the ASO or the AR. In some examples the nucleotide sequence of the ASO or AR comprises or consists of any one of SEQ ID NOs:2-351 or 353-362. In some examples the nucleotide sequence of the ASO or AR comprises or consists of any one of SEQ ID NOs: 17, 47, 73, 334-337, or 355-360. In some examples the nucleotide sequence of the ASO or AR comprises or consists of any one of SEQ ID NOs:334 or 335. In some examples the nucleotide sequence of the ASO or AR comprises or consists of any one of SEQ ID NOs:355-360. In some examples the nucleotide sequence of the ASO or AR comprises or consists of any one of SEQ ID NOs:17, 73, 336, and 337. In some examples the nucleotide sequence of the ASO or AR comprises or consists of SEQ ID NO:47.

In some examples any of the foregoing ASOs include a backbone modification. In some examples the backbone modification includes a phosphorothioate linkage or a phosphorodiamidate linkage. In other examples the ASO includes a phosphorodiamidate morpholino, a locked nucleic acid, a peptide nucleic acid, or a 2'-O-modification such as a 2'-O-methyl, a 2'-Fluoro, or a 2'-O-methoxyethyl moiety. In some examples the ASO includes at least one modified sugar moiety. In other examples each sugar moiety in the ASO is a modified sugar moiety. In some examples the ASO includes a 2'-O-methoxyethyl moiety. In other examples each nucleotide of the ASO includes a 2'-O-methoxyethyl moiety.

In some examples of any of the foregoing ASOs or vectors, the nucleotide sequence of the ASO or AR consists of 20 to 30 nucleotides, 22 to 30 nucleotides, 24 to 30 nucleotides, 25 to 30 nucleotides, or 26 to 30 nucleotides. In some examples the nucleotide sequence of the ASO or the AR consists of 25 to 30 nucleotides. In some examples, where the sequence of the ASO consists of 20 to 30 nucleotides, the ASO includes one or more phosphorodiamidate morpholino moieties.

In some examples any of the foregoing ASOs also includes a linked functional moiety. In some examples the functional moiety includes a delivery moiety. In some examples the delivery moiety is selected from the group consisting of: lipids, peptides, carbohydrates, polyethers (e.g., polyethylene glycol), and antibodies. In some examples, wherein the ASO includes a delivery moiety, the delivery moiety includes a cell-penetrating peptide (CPP). In some examples the delivery moiety includes a receptor binding domain (RBD). In some examples the delivery moiety includes a poly(ethylene glycol) (PEG) moiety. In some examples the delivery moiety includes a N-acetylgalactosamine (GalNAc) moiety. In some examples the delivery moiety includes a fatty acid or lipid moiety. In some embodiments the fatty acid chain length is about C8 to C20. In other examples the functional moiety includes a stabilising moiety. In some examples the functional moiety is covalently linked to the ASO. In other examples the functional moiety is non-covalently linked to the ASO. In some examples the functional moiety is linked to the 5' end of the ASO. In other examples the functional moiety is linked to the 3' end of the ASO.

In a related aspect provided herein is a pharmaceutical composition that includes any of the foregoing ASOs or vectors and a pharmaceutically acceptable excipient.

In a further related aspect provided herein is a method for treating autosomal ADPKD where a subject in need thereof is administered a therapeutically effective amount of the foregoing pharmaceutical composition. In some examples the subject to be treated is a human subject. In another related aspect provided herein is the use of a any of the foregoing ASOs, vectors in the manufacture of a medicament for treating ADPKD.

In another aspect provided herein is a method for increasing PKD1 mRNA and/or Polycystin 1 protein in a cell ex vivo or in a tissue in vivo, where the method includes a step of contacting the cell or tissue with any of the foregoing ASOs, vectors, or pharmaceutical compositions.

In yet another aspect provided herein is a genetically modified cell comprising any of the foregoing ASOs or vectors. In some examples the genetically modified cells are mammalian cells. In some examples the genetically modified mammalian cell is a genetically modified human cell.

BRIEF DESCRIPTION OF THE ACCOMPANYING DRAWINGS

FIG. 1—Schematic illustration of PKD1 exon-intron structure, miRNA binding sites in PKD 3' UTR, and relative binding positions of exemplary PMOs. (A) Exon/-Intron map of human PKD1 pre-mRNA; (B) sequence of PKD1 mRNA 3' UTR that includes binding site (bold) for miR-17 family miRNAs. The relative positions of complementary PMOs having sequences corresponding to SEQ ID NOs:47 (+604+628), 334 (+611+635), and 335 (+615+639), respectively, are indicated; (C) sequence of PKD1 mRNA 3' UTR including binding sites (bold) for miR-200 family miRNAs. The relative positions of complementary PMOs having sequences corresponding to SEQ ID NOs:14 (+505+529), 337 (+515+539), 336 (+677+701), 73 (+682+706) and 75 (+688+712), respectively, are indicated.

Figure 2:
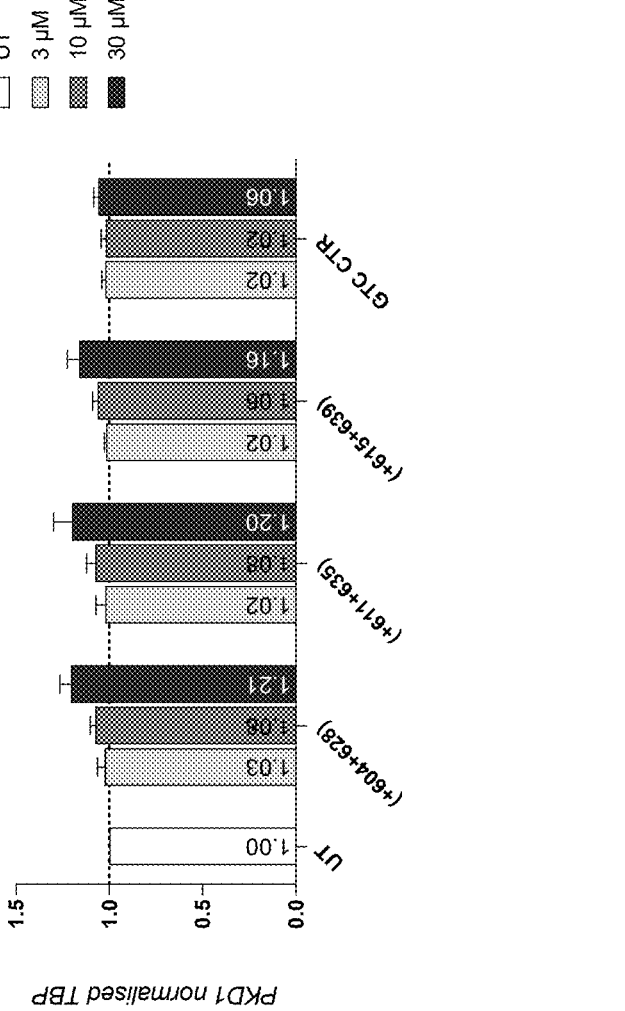

FIG. 2—Screening of PPMOs that target the miR-17 binding site in PKD1 in HEK293 cells.

Screening of PPMOs with sequences corresponding to SEQ ID NOs:47 (+604+628), 334 (+611+635), and 335 (+615+639) in HEK293 cells. The graph shows PKD1 mRNA expression at 24 h post treatment with miR-17 site targeting PPMOs or non-target control (GTC CTR). The PKD1 mRNA expression was normalized to TBP and expression in untreated cells was set to 1.

Figure 3:
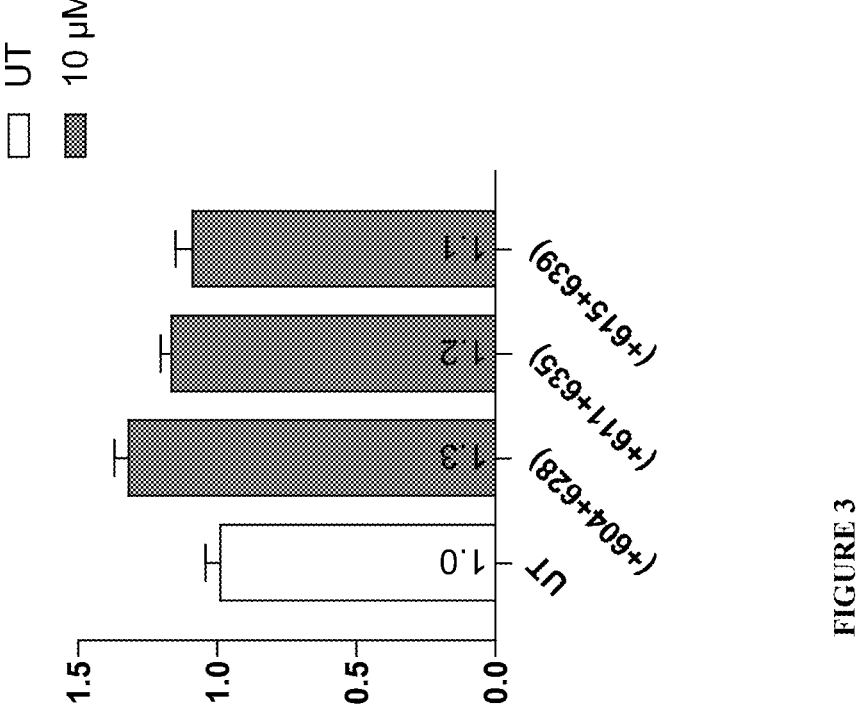

FIG. 3—Effect of PPMOs that target the sequence in the 3' UTR of PKD1 to which the miR-17 miRNA seed sequence binds in an ADPKD patient cell line PPMOs that demonstrated significant PKD1 mRNA upregulation, as per Example 2, were selected for their ability to upregulate Polycystin 1 (PC1) protein in an ADPKD patient cell line carrying the PKD1 heterozygous mutation (p.Q2556*). The graph shows the median fluorescence intensity (MFI) of PC1 protein staining on the cell surface, measured via flow cytometry 5 days post treatment with 10 μM miR-17 site targeting PPMOs. The Polycistin protein staining MFI was normalize to Isotype stained antibody controls and the MFI in untreated cells was set to 1.

Figure 4:
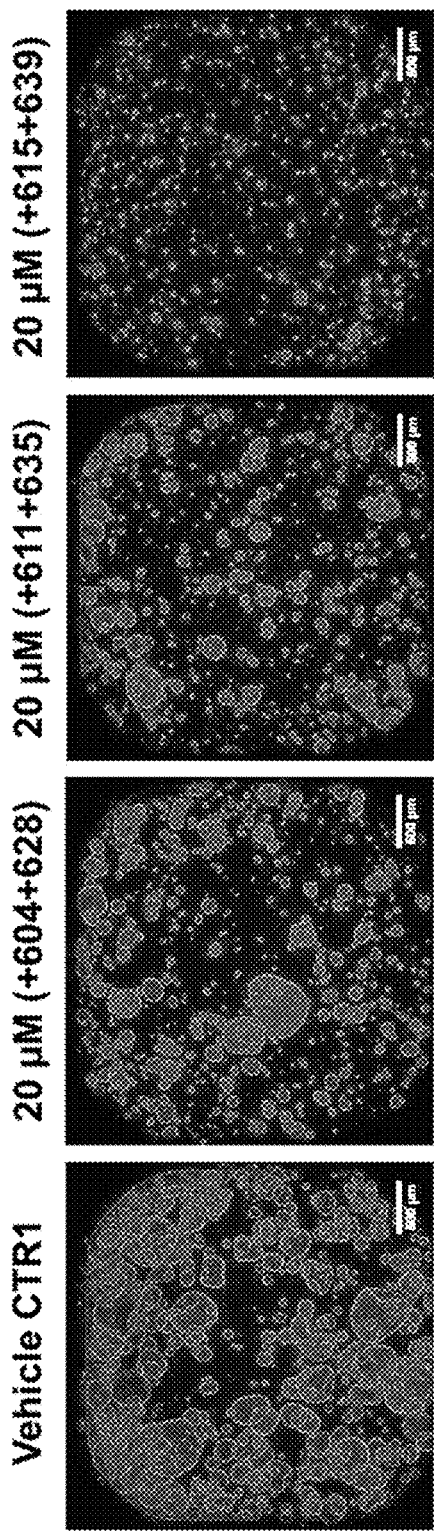

FIG. 4—Functional validation of PPMOs in a patient-derived 3D cyst model.

Functional validation of peptide PMOs (PPMOs) with sequences corresponding to SEQ ID NOs:47 (+604+628), 334 (+611+635), and 335 (+615+639) in patient derived cyst cells. The PPMOs were dosed at 1 μM, 3 μM, 10 μM and 20 μM and after 7 days of exposure, cultures were fixed and stained for actin cytoskeleton and nuclei. Growth and swelling of cysts are visualized by high-content microscopy imaging. Representative images show the cyst size in wells treated with 20 μM PPMO 7 days post treatment. The assay was performed under unstimulated condition (spontaneous cyst formation).

FIG. 5—Quantification of patient-derived 3D cyst area and cell death

Images from all assay conditions described in FIG. 4 were further analysed to determine the dose-dependent change of cyst area (μm²) and cell death (%) to distinguish the efficacy and cytotoxicity. The cut-off for cell death was set at 15%.

(A-C) Swelling Inhibition was determined from measurements of Cyst Area. This was calculated as the average area of each cyst in every plane of the z-stack. (D-F) Cytotoxicity was calculated as the proportion of dead cells. Cells were scored as 'dead' if their nucleus was not associated with a colocalizing actin cytoskeleton (rhodamine-phalloidin labelled). This value was normalized to the solvent control (0%) and presented as mean of replicates +/−standard deviation.

Figure 6:
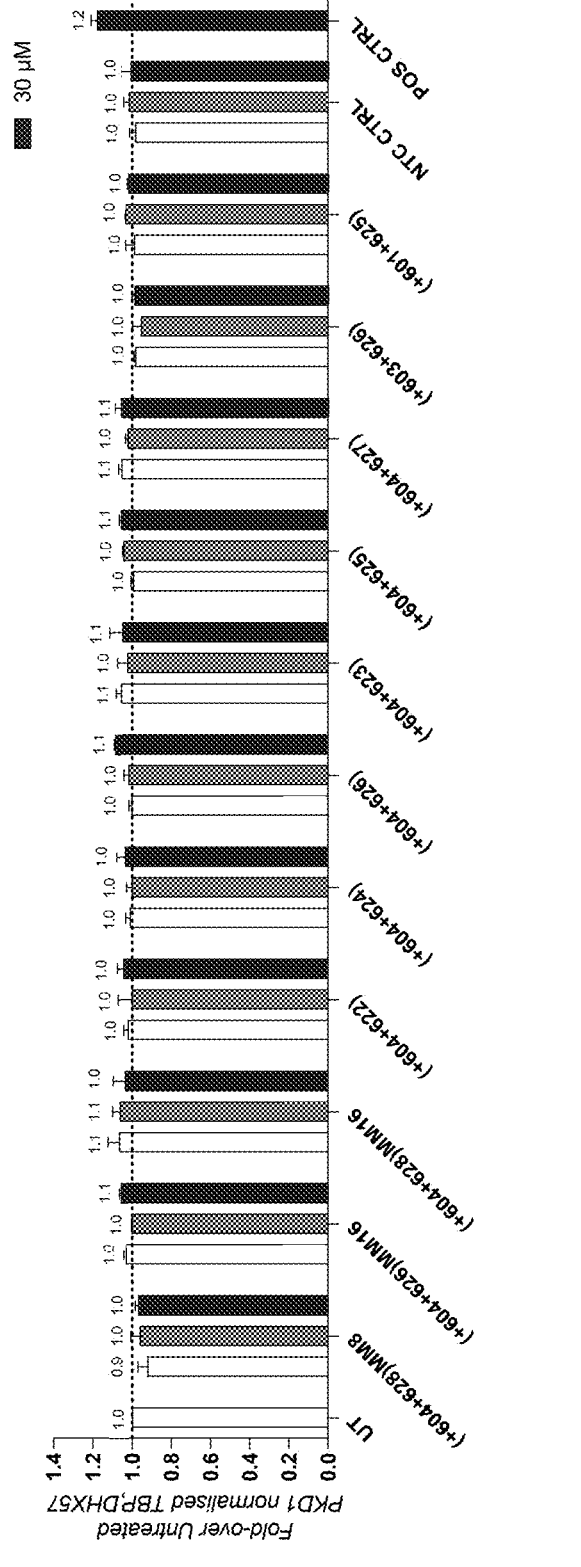

FIG. 6 Screening of PPMO microwalks for inhibition of miR-17 binding

PPMOs corresponding to oligo sequences in SEQ ID NOs:353-361, were incubated with HEK293 cells at concentrations of 3 μM, 10 μM, and 30 μM for 24 hours, with n=3 technical replicates per treatment condition. A non-targeting control PPMO, designed not to hybridize to any known human transcripts, was used as a negative control treatment. This control PPMO was conjugated to the same cell-penetrating peptide as the test PPMOs. A positive control oligonucleotide (RGLS4326, Med Chem Express, Catalogue No. HY-139290), an inhibitor of miR-17, was also included as an assay control. Data were normalized to two housekeeping genes, reported as relative levels compared to untreated cells, which were set to 1. Data represent mean±S.D. and UT=untreated cells. n=1 biological replicates. TBP=TATA-Binding Protein, DHX57=DExH-Box Helicase 57.

FIG. 7: Screening of PPMOs for inhibition of miR-200 binding

PPMOs corresponding to oligonucleotide sequences in SEQ ID NOs:14, 73, 75, 336-337 were incubated with HEK293 cells at concentrations of 3 μM, 10 μM, and 30 μM for 24 hours, with n=3 technical replicates per treatment condition. A non-targeting control PPMO, designed not to hybridize to any known human transcripts, was used as a negative control treatment. This control PPMO was conjugated to the same cell-penetrating peptide as the test PPMOs. A positive control oligo (RGLS4326, Med Chem Express, Catalogue No. HY-139290), an inhibitor of miR-17, was also included. Data were normalized to two housekeeping genes, reported as relative levels compared to untreated cells, which were set to 1. Data represent mean±S.D. and UT=untreated cells. n=2 biological replicates. TBP=TATA-Binding Protein, DHX57=DExH-Box Helicase 57.

Figure 8:
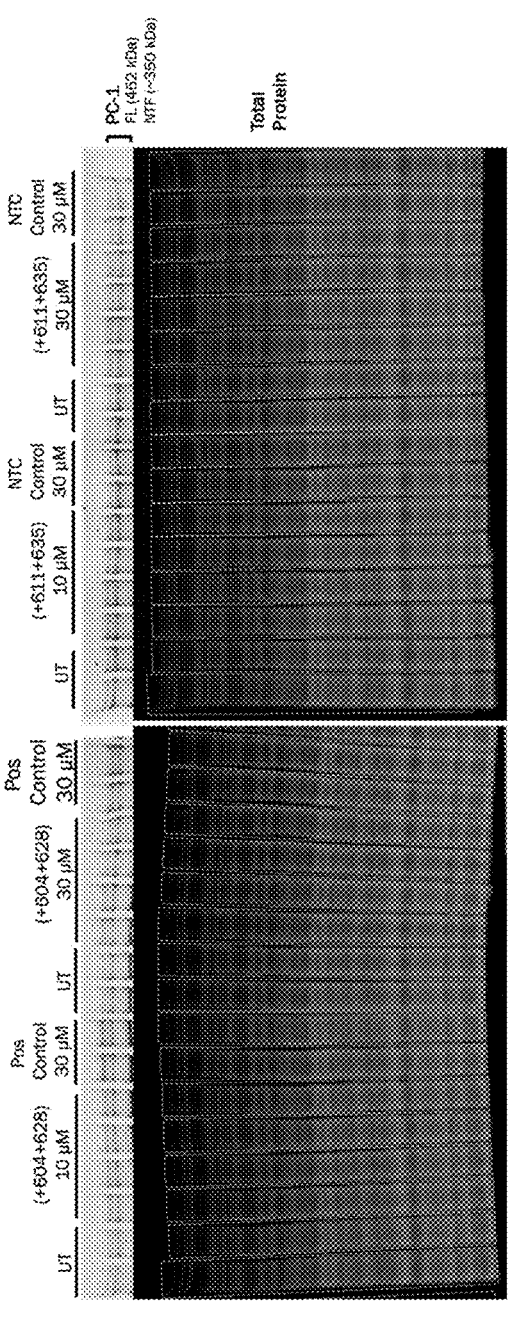

FIG. 8: Western blot images of PPMO-treated HEK293 cells

HEK293 cells were treated with PPMOs (+604+628) and (+611+635) with the sequences corresponding to SEQ ID NOs:47, and 334, respectively. A non-targeting control (NTC) was used as a negative control while an inhibitor of miR-17 (RGLS4326, Med Chem Express, Catalogue No. HY-139290), was included as a positive control. PPMO-treated cells were harvested at 5 days and analysed for PC1 expression using western blot assay. Two protein bands at approximately 462 and 350 kDa indicate full-length (FL) and N-terminal fragment (NTF) of PC1, respectively. The intensity of total protein stain was analysed as loading control. Experiment was performed in quadruplicate.

Figure 9:
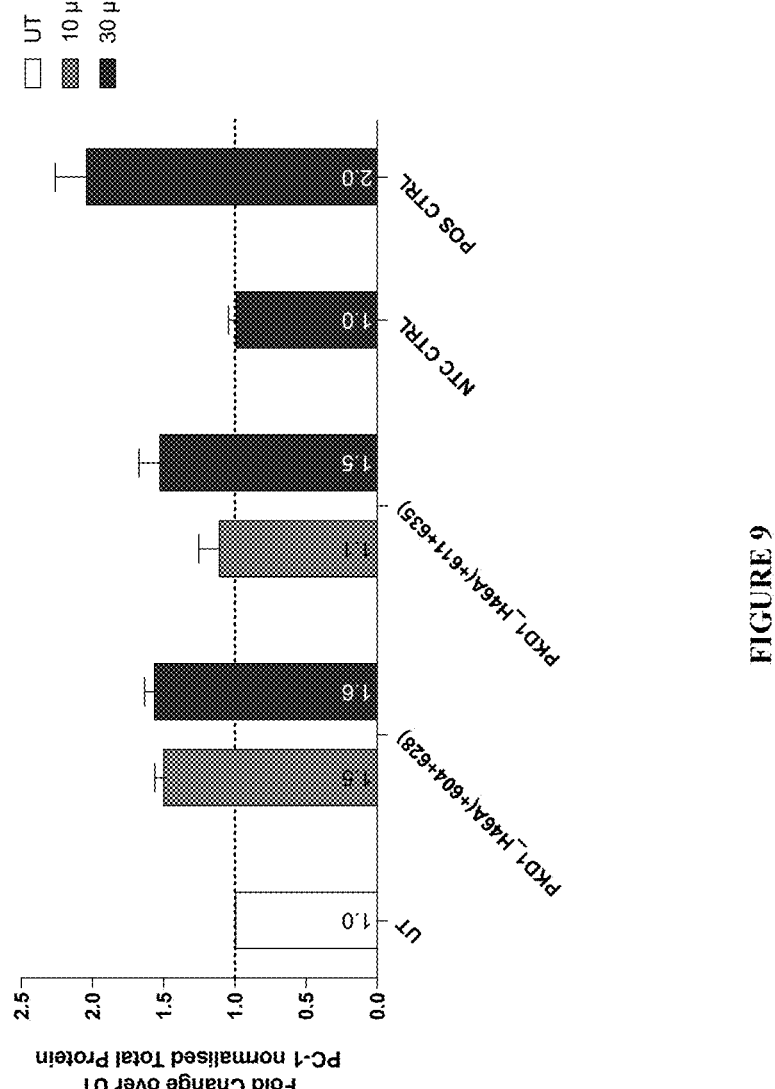

FIG. 9: Quantification of PCI protein upregulation in PPMO-treated HEK293 cells

Bar graph represents mean±S.D. of PCI protein expression analysed using gel images. Both FL and NTF bands were included in the analysis and normalized to total protein staining. A dash line indicates baseline PC1 protein level of untreated which was set as 1. Experimental was performed in quadruplicate. n=2 biological replicates. UT=untreated cells. NTC=non-targeting control.

Figure 10:
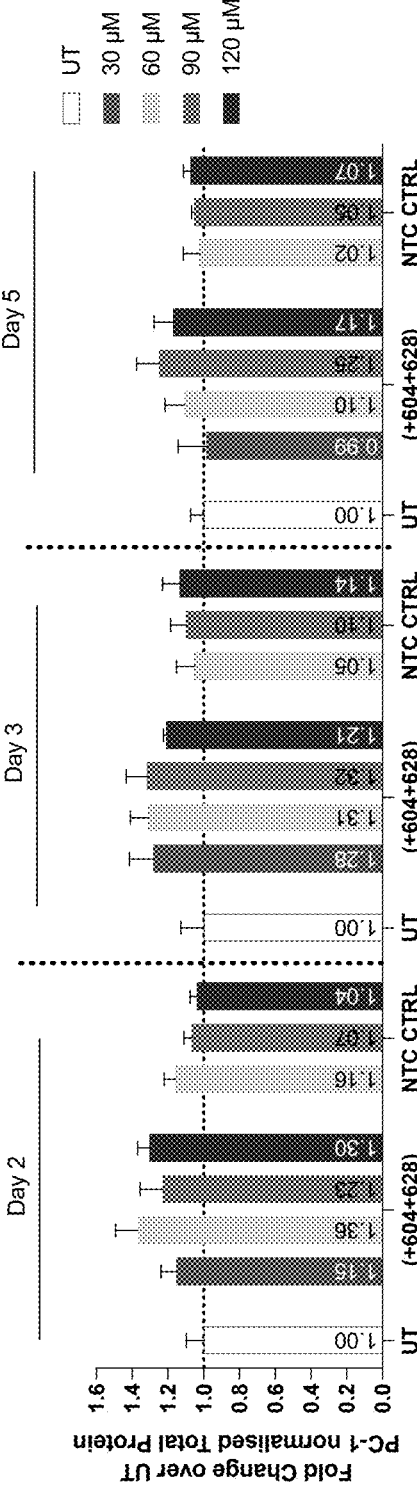

FIG. 10: PC1 protein analysis in PPMO-treated WT9-7 cells

WT9-7 cells were incubated with PPMOs with the sequences corresponding to SEQ ID NO:47 (+604+628) in quadruplicate and a non-targeting control (NTC) for 2, 3 or 5 days. A non-targeting control (NTC) was used as a negative control and an inhibitor of miR-17 (RGLS4326, Med Chem Express, Catalogue number HY-139290), was included as a positive control. Bar graph represents mean+ S.D. of PC1 protein normalized to total protein stain in relative to untreated cells. n=1 biological replicate. UT=untreated cells. NTC=non-targeting control.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such techniques are described and explained throughout the literature in sources such as Perbal 1984, Sambrook et al., 2001, Brown (editor) 1991, Glover and Hames (editors) 1995 and 1996, Ausubel et al. including all updates until present, Coligan et al. (editors) (including all updates until present), Maniatis et al. 1982, Gait (editor) 1984, Hames and Higgins (editors) 1984, Freshney (editor) 1986.

The term "and/or", e.g., "X and/or Y" shall be understood to mean either "X and Y" or "X or Y" and shall be taken to provide explicit support for both meanings or for either meaning.

The term "about", unless stated to the contrary, refers to +/−20%, more preferably +/−10%, of the designated value. For the avoidance of doubt, the term "about" followed by a designated value is to be interpreted as also encompassing the exact designated value itself (for example, "about 10" also encompasses 10 exactly).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "antisense oligonucleotide" "antisense oligomer" or "ASO," as used herein, encompasses oligonucleotides and any other oligomeric molecule that comprises nucleobases capable of hybridizing to a complementary sequence on a target RNA transcript, including, but not limited to, those that do not comprise a sugar moiety, such as in the case of a peptide nucleic acid (PNA). Preferably, the ASO is an ASO that is resistant to nuclease cleavage or degradation.

The phrase "binds to a targeted portion" or "binds within a targeted portion," in reference to an ASO or AR, as used herein, refers to specific hybridization between the ASO or AR nucleotide sequence and a target nucleotide sequence that is complementary within the ranges set forth herein. In some examples, specific hybridization occurs where, under ex vivo conditions, the hybridization occurs under high stringency conditions. By "high stringency conditions" is meant that the ASO or AR, under such ex vivo conditions, hybridize to a target sequence in an amount that is detectably stronger than non-specific hybridization. High stringency conditions, then, are conditions that distinguish a polynucleotide with an exact complementary sequence, or one containing only a few scattered mismatches from a random sequence that happened to have a few small regions (e.g., 1-5 bases) that matched the probe. Such small regions of complementarity are more easily melted than a full-length complement of 12-17 or more bases, and moderate stringency hybridization makes them easily distinguishable. In one example, high stringency conditions include, for example, low salt and/or high temperature conditions, such as provided by about 0.02-0.1 M NaCl or the equivalent, at temperatures of about 50-70° C. The skilled person will appreciate that under in vivo conditions, the specificity of hybridization between an ASO or an AR and its target sequence is defined in terms of the level of complementarity between the ASO or an AR and the target sequence to which it hybridizes within a cell.

The term "peptide" is intended to include compounds composed of amino acid residues linked by amide bonds. A peptide may be natural or unnatural, ribosome encoded or synthetically derived. Typically, a peptide will consist of between 2 and 200 amino acids. For example, the peptide may have a length in the range of 10 to 20 amino acids or 10 to 30 amino acids or 10 to 40 amino acids or 10 to 50 amino acids or 10 to 60 amino acids or 10 to 70 amino acids or 10 to 80 amino acids or 10 to 90 amino acids or 10 to 100 amino acids, including any length within said range(s). The peptide may comprise or consist of fewer than about 150 amino acids or fewer than about 125 amino acids or fewer than about 100 amino acids or fewer than about 90 amino acids or fewer than about 80 amino acids or fewer than about 70 amino acids or fewer than about 60 amino acids or fewer than about 50 amino acids.

Peptides, as referred to herein, include "inverso" peptides in which all L-amino acids are substituted with the corresponding D-amino acids, "retro-inverso" peptides in which the sequence of amino acids is reversed and all L-amino acids are replaced with D-amino acids.

Peptides may comprise amino acids in both L- and/or D-form. For example, both L- and D-forms may be used for different amino acids within the same peptide sequence. In some examples the amino acids within the peptide sequence are in L-form, such as natural amino acids. In some examples the amino acids within the peptide sequence are a combination of L- and D-form. Further, peptides may comprise unusual, but naturally occurring, amino acids including, but not limited to, hydroxyproline (Hyp), beta-alanine, citrulline (Cit), ornithine (Orn), norleucine (Nle), 3-nitrotyrosine, nitroarginine, pyroglutamic acid (Pyr). Peptides may also incorporate unnatural amino acids including, but not limited to, homo amino acids, N-methyl amino acids, alphamethyl amino acids, beta (homo) amino acids, gamma amino acids, and N-substituted glycine. Peptides may be linear peptides or cyclic peptides.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical bond or a disulfide bond. Examples of non-covalent bonds include hydrogen bonds, ionic bonds, Van der Waals forces, and hydrophobic interactions.

Percentage amino acid sequence identity with respect to a given amino acid sequence is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Amino acid sequence identity may be determined using the EMBOSS Pairwise Alignment Algorithms tool available from The European Bioinformatics Institute (EMBL-EBI), which is part of the European Molecular Biology Laboratory. This tool is accessible at the website located at. This tool utilizes the Needleman-Wunsch global alignment algorithm (Needleman and Wunsch, 1970). Default settings are utilized which include Gap Open: 10.0 and Gap Extend 0.5. The default matrix "Blosum62" is utilized for amino acid sequences and the default matrix.

The term "cell penetrating peptide" (CPP) refers to a peptide that is capable of crossing a cellular membrane. In one example, a CPP is capable of translocating across a mammalian cell membrane and entering into a cell. In another example, a CPP may direct a conjugate to a desired subcellular compartment. Thus, a CPP may direct or facilitate penetration of a molecule of interest across a phospholipid, mitochondrial, endosomal, lysosomal, vesicular, or nuclear membrane. A CPP may be translocated across the membrane with its amino acid sequence complete and intact, or alternatively partially degraded.

A CPP may direct a molecule of interest, such as an ASO disclosed herein, from outside a cell through the plasma membrane, and into the cytoplasm or a desired subcellular compartment. Alternatively, or in addition, a CPP may direct a molecule of interest across the, epithelial, endothelial, basement membrane, trans-mucosal, cardiovascular, skin, gastrointestinal and/or pulmonary barriers. In some embodiments the CPP is selectively targeted to or taken up by the kidneys.

The term "peptide ligand" or "receptor binding domain" refers to a peptide that is capable of binding to a membrane surface receptor to enable translocation of the peptide across a cellular membrane. In one example a peptide ligand may enable translocation across the cellular membrane via the natural endocytosis of the targeted receptor. In another example the peptide ligand may utilise a complementary mechanism of translocation across the cellular membrane including utilising a conjugated CPP. In one example, a peptide ligand is capable of translocating across a mammalian cell membrane and to enter a cell. In another example, a peptide ligand may direct a conjugate to a desired subcellular compartment. Thus, a peptide ligand may direct or facilitate cellular uptake of a molecule of interest across a phospholipid, mitochondrial, endosomal, lysosomal, vesicular, or nuclear membrane. A peptide ligand may be translocated across the membrane with its amino acid sequence complete and intact, or alternatively partially degraded.

A peptide ligand via its binding to a target receptor may direct a molecule of interest, such as an ASO disclosed herein, from outside a cell through the plasma membrane, and into the cytoplasm or a desired subcellular compartment. Alternatively, or in addition, a peptide ligand via its binding to a target receptor may direct a molecule of interest across a relevant biological barrier, e.g., the renal basement membrane, blood-brain, trans-mucosal, hematoretinal, cardiovascular, skin, gastrointestinal, and/or pulmonary barriers.

Compositions for Increasing PKD1 mRNA and Polycystin-1 Protein Levels

MicroRNAs (miRNAs) are a family of short (19 to 23 nucleotide) non-coding single stranded labile RNAs. Although they can bind to any part of target mRNA, their main mode of action is to bind to complimentary RNA sequences in the 3' untranslated region (3' UTR) and regulate gene expression by stimulating either mRNA degradation or translational repression. Both mechanisms lead to diminished expression of the target gene. In the case of the Polycystic Kidney Disease 1 (PKD 1) gene that encodes Polycystin 1 protein, miRNAs that bind to the 3' UTR and of the encoding mRNA transcript include miR-17 family miRNAs (e.g., miR-17-5p, miR-106a-5p, miR-106b-5p, miR-20a-5p, miR-93-5p) and miR-200 family miRNAs (e.g., miR-200b, miR200c, or miR-429).

While not wishing to be bound by theory, it is believed that an antisense sequence at least partly complementary to the binding sites for microRNAs located within the PKD1 mRNA 3' UTR will hybridize to the PKD1 3' UTR and sterically hinder ("mask") access of these miRNAs to their binding sites on the PKD1 3' UTR, ultimately allowing increases in Polycystin 1 protein levels.

Accordingly, disclosed herein is an ASO that binds to a targeted portion of the 3' UTR of a PKD1 mRNA wherein binding of the antisense oligonucleotide to the targeted portion increases the level of PKD1 mRNA and/or Polycystin 1 protein. In some preferred examples the ASO hybridizes to a targeted portion of the 3' UTR of PKD1 mRNA, whereby one or more miRNAs are unable to hybridize to their specific target sequences and consequently, increased levels of PKD1 mRNA and Polycystin 1 protein.

Also disclosed herein is a vector for expression, in a mammalian cell, of an AR that binds to a targeted portion of the 3' UTR of PKD1 mRNA ultimately resulting in increased levels of Polycystin 1 protein as described above.

For reference, the sequence of the canonical human PKD1 mRNA transcript ("PKD-201") is publicly available through the online Ensembl database under record ENST00000262304.9. The nucleotide sequence of the canonical human PKD1 mRNA 3' UTR sequence is provided herein as SEQ ID NO:1.

Antisense Oligonucleotides (ASOs) and Antisense RNAs (ARs)

In some preferred examples of the compositions and methods described herein, ASOs and ARs have a sequence that is completely complementary across its length to the target sequence or a sequence near complementarity (e.g., sufficient complementarity to bind the target sequence and interfere with miRNA binding at the PKD1 mRNA 3' UTR binding site). ASOs and ARs are designed so that they bind (hybridize) to a target RNA sequence (e.g., a targeted portion of a pre-mRNA transcript) and remain hybridized under physiological conditions. Selection of suitable sequences for ASOs and ARs generally avoids, where possible, similar nucleic acid sequences in other (i.e., off-target) locations in the genome or in cellular mRNAs or miRNAs, such that the likelihood the ASO or AR will hybridize at such sites is limited.

In some examples, ASOs or ARs "specifically hybridize" to or are "specific" to a target nucleic acid or a targeted portion of the PKD1 mRNA 3' UTR. At a given ionic strength and pH, the $T_m$ is the temperature at which 50% of a target sequence hybridizes to a complementary oligonucleotide.

ASO and AR sequences are "complementary" to their target sequences when hybridization occurs in an antiparallel configuration between two single-stranded polynucleotides of complementary sequence. Complementarily is quantifiable in terms of the proportion (e.g., the percentage) of bases in opposing strands that are expected to form hydrogen bonds with each other, according to generally accepted base-pairing rules. The nucleotide sequence of an ASO or AR need not be 100% complementary to that of its target nucleic acid to hybridize. In certain examples, the nucleotide sequences of ASOs or ARs in the compositions disclosed herein can be at least 60%, at least 65%, at least 70%, at least 75%, at least 80%, at least 85%, at least 90%, at least 95%, at least 96%, at least 97%, at least 98%, or at least 99% sequence complementary to the nucleotide sequence of the targeted portion of an RNA transcript over the length of the ASO or AR nucleotide sequence. For example, an ASO or AR in which 18 of 20 nucleotides of ASO or AR sequence are complementary to a target region, and would therefore specifically hybridize, would represent 90 percent complementarity. In such an example, the remaining non-complementary nucleotides of the ASO or AR could be clustered together or interspersed with complementary nucleotides and need not be contiguous. Complementarity of an ASO or AR sequence to a target nucleotide sequence (expressed as "percent complementarity" to its target sequence; or "percent identity" to its reverse complement sequence) can be determined routinely using algorithms known in the art, as exemplified in the BLAST programs (basic local alignment search tools) and Power-BLAST programs (Altschul, et al., 1990, J Mol. Biol., 215:403-410; Zhang et al., 1997, *Genome Res.,* 7:649-656).

In some examples, an ASO or AR does not hybridize to all nucleotides in a target sequence and the nucleotide positions at which it does hybridize may be contiguous or non-contiguous. ASOs or ARs may hybridize over one or more segments of a 3' UTR region of a mRNA, such that intervening or adjacent segments are not involved in the hybridization event (e.g., a loop structure or hairpin structure may be formed).

In some examples the nucleotide sequences of ASOs or ARs described herein are complementary to a targeted portion of PKD1 mRNA 3' UTR. In some preferred examples, the ASOs or ARs are complementary to a targeted portion of the PKD1 mRNA 3' UTR corresponding to SEQ ID NO:1. In some examples the nucleotide sequence of the ASO or the AR is at least 60%, 65%, 70%, 75%, 80%, 85%, 90%, 95%, or 100% complementary to the nucleotide sequence of the targeted portion of the PKD1 3' UTR over the length of the ASO or the AR. In some examples the nucleotide sequence of the ASO or the AR is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, over the entire length of any of the sequences provided in SEQ ID NOs: 2-351 or 353-362 (shown in Table 1).

The ASOs or ARs for use in the compositions described herein may be of any length suitable for specific hybridization to a target sequence. In some examples, the nucleotide sequence of the ASOs or ARs consist of 8 to 50 nucleotides. For example, the ASO or AR sequence can be 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleotides in length. In some examples, the ASOs consist of more than 50 nucleotides, but no more than 100 nucleotides in length. In some examples, the ASO or AR nucleotide sequence is from 8 to 50 nucleotides, 8 to 40 nucleotides, 8 to 35 nucleotides, 8 to 30 nucleotides, 8 to 25 nucleotides, 8 to 20 nucleotides, 8 to 15 nucleotides, 9 to 50 nucleotides, 9 to 40 nucleotides, 9 to 35 nucleotides, 9 to 30 nucleotides, 9 to 25 nucleotides, 9 to 20 nucleotides, 9 to 15 nucleotides, 10 to 50 nucleotides, 10 to 40 nucleotides, 10 to 35 nucleotides, 10 to 30 nucleotides, 10 to 25 nucleotides, 10 to 20 nucleotides, 10 to 15 nucleotides, 11 to 50 nucleotides, 11 to 40 nucleotides, 11 to 35 nucleotides, 11 to 30 nucleotides, 11 to 25 nucleotides, 11 to 20 nucleotides, 11 to 15 nucleotides, 12 to 50 nucleotides, 12 to 40 nucleotides, 12 to 35 nucleotides, 12 to 30 nucleotides, 12 to 25 nucleotides, 12 to 20 nucleotides, 12 to 15 nucleotides, 13 to 50 nucleotides, 13 to 40 nucleotides, 13 to 35 nucleotides, 13 to 30 nucleotides, 13 to 25 nucleotides, 13 to 20 nucleotides, 14 to 50 nucleotides, 14 to 40 nucleotides, 14 to 35 nucleotides, 14 to 30 nucleotides, 14 to 25 nucleotides, 14 to 20 nucleotides, 15 to 50 nucleotides, 15 to 40 nucleotides, 15 to 35 nucleotides, 15 to 30 nucleotides, 15 to 25 nucleotides, 15 to 20 nucleotides, 20 to 50 nucleotides, 20 to 40 nucleotides, 20 to 35 nucleotides, 20 to 30 nucleotides, 20 to 25 nucleotides, 25 to 50 nucleotides, 25 to 40 nucleotides, 25 to 35 nucleotides, or 25 to 30 nucleotides in length. In some examples, the ASOs or ARs are 20 nucleotides in length. In some preferred examples, the nucleotide sequence of the ASO or AR nucleotide is 25 nucleotides in length.

In some examples for each occurrence of "G" in an ASO or AR sequence disclosed herein, the "G" is guanosine or inosine. In some examples for each occurrence of "T" in an ASO or AR sequence disclosed herein, the "T" is any one of: thymidine, inosine, uracil, or an isomeric or modified form of uracil (e.g., pseudouridine or N1-methyl-pseudouridine). In some examples for each occurrence of "C" in an ASO or AR sequence disclosed herein, the C is cytosine or a modified form of cytosine (e.g., 5'-methyl cytosine).

In some examples the nucleotide sequence of the ASO or AR comprises the sequence of any one of SEQ ID NOs:2-351 or 353-362. In some examples the nucleotide sequence of the ASO or AR consists of the sequence of any one of SEQ ID NOs:2-351 or 353-362. In some examples the nucleotide sequence of the ASO or AR comprises or consists of the sequence of any one of SEQ ID NOs:17, 47, 73, 334-337, or 355-360. In some examples the nucleotide sequence of the ASO or AR comprises or consists of the sequence of any one of SEQ ID NOs:334 or 335. In some examples the nucleotide sequence of the ASO or AR comprises or consists of the sequence of any one of SEQ ID NOs:355-360. In some examples the nucleotide sequence of the ASO or AR comprises or consists of the sequence of any one of SEQ ID NOs:17, 73, 336, and 337. In some examples the nucleotide sequence of the ASO or AR comprises or consists of SEQ ID NO:47.

ASO Chemistry and Modifications

The ASOs used in the compositions described herein may comprise naturally-occurring nucleotides, nucleotide analogues, modified nucleotides, or any combination thereof. The term "naturally occurring nucleotides" includes deoxyribonucleotides and ribonucleotides. The term "modified nucleotides" includes nucleotides with modified or substituted sugar groups and/or having a modified backbone. In some examples, all the nucleotides of an ASO are modified nucleotides. Chemical modifications of ASOs or components of ASOs that are compatible with the compositions and methods described herein are known in the art as disclosed in, e.g., in U.S. Pat. Nos. 8,258,109, 5,656,612, U.S. Patent Publication No. 2012/0190728, and Roberts et al., 2020, *Nature Rev. Drug Disc.,* 19:673-694.

One or more nucleotides of an ASO may be any naturally occurring, unmodified nucleobase such as adenine, guanine, cytosine, thymine, uracil and inosine, or any synthetic or modified nucleobase that is sufficiently similar to an unmodified nucleobase such that it is capable of hydrogen bonding with a nucleobase present on a target RNA transcript. Examples of suitable modified nucleobases include, but are not limited to, hypoxanthine, xanthine, 7-methylguanine, 5, 6-dihydrouracil, 5-methylcytosine, and 5-hydroxymethoylcytosine.

ASOs include a "backbone" structure, that refers to the connection between nucleotides/monomers of the ASO. In naturally occurring oligonucleotides, the backbone comprises a 3'-5' phosphodiester linkage connecting sugar moieties of adjacent nucleotides. Suitable types of backbone linkages for the ASOs described herein include, but are not limited to, phosphodiester, phosphorothioate, phosphoroselenoate, phosphorodiselenoate, phosphorodithioate, phosphorodiamidate, phosphoroanilothioate, phosphoranilidate, phosphoramidate, and the like. In some examples, the backbone modification is a phosphorothioate linkage. In other examples, the backbone modification is a phosphorodiamidate linkage. See, e.g., Roberts et al. supra; and Agrawal (2021), Biomedicines, 9:503. In some examples, the backbone structure of the ASO does not contain phosphorous-based linkages, but rather contains peptide bonds, for example in a peptide nucleic acid (PNA), or linking groups including carbamate, amides, and linear and cyclic hydrocarbon groups.

In some examples, the stereochemistry at each of the phosphorus internucleotide linkages of the ASO backbone is random. In other examples, the stereochemistry at each of the phosphorus internucleotide linkages of the ASO backbone is controlled and is not random. For example, U.S. Pat. No. 9,605,019 describes methods for independently selecting the handedness of chirality at each phosphorous atom in an oligonucleotide. In some examples, an ASO used in the compositions and methods provided herein, including, but not limited to, the ASOs the sequences of which are disclosed herein as SEQ ID NOs:2-351 is an ASO having phosphodiester internucleotide linkages that are not random. In some examples, a composition or composition used in the methods disclosed herein comprises a pure diastereomeric ASO. In other examples, the composition comprises an ASO that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In some examples, the ASO has a non-random mixture of Rp and Sp configurations at its phosphorus internucleotide linkages. In some examples, an ASO used in the compositions and methods disclosed herein, comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp.

In some examples, the ASOs described herein contain a sugar moiety that comprises ribose or deoxyribose, or a modified sugar moiety or sugar analogue, including a morpholine ring.

Suitable examples of modified sugar moieties include, but are not limited to, 2' substitutions such as 2'-O-modifications, 2'-O-methyl (2'-O-Me), 2'-O-methoxyethyl (2'MOE), 2'-O-aminoethyl, 2'F, N3'→P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some examples, the sugar moiety modification is selected from among 2'-O-Me, 2'F, and 2'MOE. In other examples, the sugar moiety modification is an extra bridge bond, such as in a locked nucleic acid (LNA). In some examples the sugar analogue contains a morpholine ring, such as phosphorodiamidate morpholino (PMO). In some examples, the sugar moiety comprises a ribofuransyl or 2'deoxyribofuransyl modification. In some examples, the sugar moiety comprises 2'4'-constrained 2'-O-methyloxyethyl (cMOE) modifications. In some examples, the sugar moiety comprises cEt 2', 4' constrained 2'-0 ethyl BNA modifications. In other examples, the sugar moiety comprises tricycloDNA (tcDNA) modifications. In some examples, the sugar moiety comprises ethylene nucleic acid (ENA) modifications. In some examples, the sugar moiety comprises 2'-O-(2-N-methylcarbamoylethyl) (MCE). Modifications are known in the art as exemplified in Jarver, et al., 2014, Nucleic Acid Therapeutics, 24(1): 37-47.

In some examples, each constituent nucleotide of the ASO is modified in the same way, e.g., every linkage of the backbone of the ASO comprises a phosphorothioate linkage, or each ribose sugar moiety comprises a 2'-O-methyl modification. In other examples, a combination of different modifications is used, e.g., an ASO comprising a combination of phosphorodiamidate linkages and sugar moieties comprising morpholine rings (morpholinos).

In some examples, the ASO comprises one or more backbone modifications. In some examples, the ASO comprises one or more sugar moiety modification. In some examples, the ASO comprises one or more backbone modifications and one or more sugar moiety modifications. In some examples, the ASO comprises a 2'-O-MOE modification and a phosphorothioate backbone. In some examples, the ASO comprises a peptide nucleic acid (PNA).

In some preferred examples, the ASO comprises a phosphorodiamidate morpholino (PMO).

The skilled person in the art will appreciate that ASOs may be modified, in order to achieve desired properties or activities of the ASO or reduce undesired properties or activities of the ASO. In some examples, an ASO is modified to alter one or more properties. For example, such modifications can: enhance binding affinity to a target sequence on a pre-mRNA transcript; reduce binding to any non-target sequence; reduce degradation by cellular nucleases (e.g., RNase H); improve uptake of an ASO into a cell and/or particular subcellular compartments; alter the pharmacokinetics or pharmacodynamics of the ASO; and/or modulate the half-life of the ASO in vivo.

In some examples, the ASOs comprise one or more 2'-O-(2-methoxyethyl) (MOE) phosphorothioate-modified nucleotides that have been shown to confer significantly enhanced resistance of ASOs to nuclease degradation and increased bioavailability.

Methods for synthesis and chemical modification of ASOs, as well as synthesis of ASO conjugates is well known in the art, and such ASOs are available commercially.

In some examples, a composition (e.g., a pharmaceutical composition) provided here includes two or more ASOs with different chemistries but complementary to the same targeted portion of the PKD1 mRNA 3' UTR. In other examples, two or more ASOs that are complementary to different targeted portions of the PKD1 mRNA 3' UTR.

In some examples, the compositions disclosed herein include ASOs that are linked to a functional moiety. In some examples, the functional moiety is a delivery moiety, a targeting moiety, a detection moiety, a stabilizing moiety, or a therapeutic moiety. In some examples the functional moiety includes a delivery moiety or a targeting moiety. In some examples the functional moiety includes a stabilizing moiety. In some preferred examples the functional moiety is a delivery moiety.

Suitable delivery moieties include, but are not limited to, lipids, peptides, carbohydrates, polyethers, and antibodies.

In some examples, the delivery moiety includes a cell-penetrating peptide (CPP).

Suitable examples of CPPs are described in, e.g., PCT/AU2020/051397. In some examples the amino acid sequence of the CPP comprises or consists of: RRSRT-ARAGRPGRNSSRPSAPR (SEQ ID NO: 352). In one example, the CPP comprises the sequence RRSRT-ARAGRPGRNSSRPSAPR (SEQ ID NO: 352), optionally wherein any amino acid other than glycine is a D amino acid. In other examples, the delivery moiety includes a receptor binding domain.

In other examples, the delivery moiety includes a carbohydrate. In some examples, a carbohydrate delivery moiety is selected from among N-acetylgalactosamine (GalNAc), N-Ac-Glucosamine (GluNAc), and a mannose. In one example, the carbohydrate delivery moiety is GalNAc.

In other examples, the delivery moiety includes a lipid. Examples of suitable lipids as delivery moieties include, but are not limited to, cholesterol moiety, a cholesteryl moiety, and aliphatic lipids. In some examples the delivery moiety includes a fatty acid or lipid moiety. In some embodiments the fatty acid chain length is about C8 to C20. Examples of suitable fatty acid moieties and their conjugation to oligonucleotides are found in, e.g., International Patent Publication WO 2019232255 and in Prakash et al., (2019).

In further examples, the delivery moiety includes an antibody, as described in, e.g., Dugal-Tessier et al., (2021).

Suitable examples of stabilizing moieties include, but are not limited to, polyethylene glycol (PEG), poly(oligo(ethylene glycol) methyl ether methacrylate) (POEGMA), and Poly(2-oxazoline)s (POx).

In some examples, where an ASO is linked to a functional moiety, the functional moiety is covalently linked to the ASO. In other examples, the functional moiety is non-covalently linked to the ASO.

Functional moieties can be linked to one or more of any nucleotides in an ASO at any of several positions on the sugar, base or phosphate group, as understood in the art and described in the literature, e.g., using a linker. Linkers can include a bivalent or trivalent branched linker. In some examples, the functional moiety is linked to the 5' end of the ASO. In other examples, the functional moiety is linked to the 3' end of the ASO.

In some examples compositions comprising any of the ASOs disclosed herein also include a delivery nanocarrier complexed with ASO. In some examples, a delivery nanocarrier is selected from among lipoplexes, liposomes, exosomes, inorganic nanoparticles, and DNA nanostructures.

In other examples the delivery nanocarrier includes a lipid nanoparticle encapsulating the ASO.

Various delivery ASO-nanocarrier complex formats are known in the art, as reviewed in, e.g., Roberts et al., supra.

Vectors for Expression of PKD1 Antisense RNA (AR)

In some examples provided herein are compositions containing a vector for expression, in a mammalian cell, of an AR that binds to a targeted portion of the PKD1 3' UTR, wherein binding of the AR to the targeted portion reduces specific binding of miRNA binding to the 3' UTR, e.g., binding of miR-17 family miRNAs (e.g., miR-17-5p, miR-106a-5p, miR-106b-5p, miR-20a-5p, miR-93-5p) or miR-200 family miRNAs (e.g., miR-200b, miR200c, or miR-429).

In some examples, the promoter used in the expression vector is a kidney cell type-selective promoter for driving expression of the AR in the mammalian cell. In some examples, the kidney cell type-selective promoter is selective for expression in a kidney cell type selected from the list consisting of: pericytes, podocytes, parietal epithelial cells, proximal tubule cells, ascending loop of Henle cells, descending loop of Henle cells, distal tubule cells, connecting tubule cells, intercalated cells, principal cells, peritubular capillary endothelium cells, and glomerular endothelium cells. For example, the sodium-dependent phosphate transporter type 2a (NPT2a) promoter for expression in the proximal tubule, the sodium-potassium-2-chloride cotransporter (NKCC2) promoter for expression in the thick ascending limb of Henle (TALH), the aquaporin 2 (AQP2) promoter for expression in the collecting duct, and the podocin promoter for expression in podocytes.

In some examples the promoter is an inducible promoter, e.g., inducible by a ligand-regulated transactivator such as the Tet-inducible rtTA that allows titration of AR transcription in a target mammalian cell. In some examples, the promoter driving AR expression is a U6 or other Pol III promoter, which is particularly suitable for transcription of short RNA sequences such AR sequences disclosed herein. In some examples, an expression vector utilizes hybrid promoter systems, e.g., a Tet-O-regulated U6 promoter system as described in Lin et al. (2004), *FEBS Letters,* 577 (2004) 376-380. In some examples, where both cell type-specificity and inducibility of an AR expression vector are desired, a two-part expression system is used in which expression of a ligand-regulated transactivator is driven by a cell type-selective promoter and expression of an AR disclosed herein is driven by a promoter regulated by the ligand-regulated transactivator.

In some examples, the expression vectors used in the compositions disclosed herein are non-viral expression vectors, e.g., plasmid vectors, minicircle DNA vectors, linear amplicon expression cassettes, and the like.

In some examples, composition containing a non-viral expression virus further comprises a transfection agent. Exemplary transfection agents for transfection include, but are not limited to, jet-PEI® (available from Polyplus-transfection® SA, Strasbourg, France); TurboFect in vivo Transfection Reagent (ThermoFisher), and cationic derivatives of polyisoprenoid alcohols (PTAI) as described in, e.g., Rak et al. (2016), *J Gene Med,* 18(11-12):331-342.

In other examples, the expression vectors to be used are viral vectors, i.e., non-replicative recombinant viruses suitable for expression of an AR disclosed herein.

Preferably, the recombinant virus for expression of the PICT1 AR is a DNA virus. Suitable types of DNA viruses include adeno-associated virus (AAV), adenovirus, lentivirus, herpes simplex virus (HSV), and anelloviruses. Methods for design, production, and use of such types of recombinant DNA viruses are established in the art, as exemplified in Fukazawa et al., (2010), *International J of Mol. Med,* 25(1), 3-10, and in "Gene Therapy Protocols" for adenovirus; "Adeno-Associated Virus: Methods and Protocols" for AAV; Cody et al (2013), *Journal of Genetic Syndromes & Gene Therapy,* 4(1), 126, and *"Herpes Simplex Virus: Methods and Protocols"* for HSV; *"Gene Therapy Protocols Vol. 1: Production and In Vivo Applications of Gene Transfer Vectors"*; and Merten et al. (2016), *Molecular Therapy Methods & Clinical Development,* 3, 16017, and Emeagi et al. (2013), *Current Molecular Medicine* 13(4), 602-625 for lentivirus. In some preferred examples, the viral vector is a recombinant AAV.

Genetically Modified Cells

Also provided herein are genetically modified cells. In some examples the genetically modified cells are genetically modified bacterial cells (e.g., recombinant *E. coli*, for amplifying an AR expression vector disclosed herein). In other examples the genetically modified cells are genetically modified mammalian cells that have been transfected with any of the ASOs or non-viral AR expression vectors; or transduced with any of the viral AR expression vectors disclosed herein. In some examples, the genetically modified mammalian cells are ex vivo, e.g., as a cultured cell population. In other examples, the genetically modified mammalian cells are in vivo, e.g., in a mouse. In some examples, the genetically modified mammalian cells are human cells.

In some examples the genetically modified mammalian cells are of primary cell types. Suitable examples of primary cell types include, but are not limited to, cyst cells, pericytes, podocytes, parietal epithelial cells, proximal tubule cells, ascending loop of Henle cells, descending loop of Henle cells, distal tubule cells, connecting tubule cells, intercalated cells, principal cells, peritubular capillary endothelium cells, and glomerular endothelium cells. In some examples such primary cell types can be obtained by differentiation of a human pluripotent stem cell line, e.g., a human induced pluripotent stem cell (hiPSC) line or a human embryonic stem cell (hESC) line. Methods for obtaining a variety of different renal cell types is known in the art, as reviewed in, e.g., de Carvalho Ribeiro et al. (2020) and Osafune et al. (2021). In some examples, the primary cell types are derived from dividing kidney tissue such as renal cysts. Cyst cells excised from ADPKD kidneys have been extensively used since the 1980s. A detailed protocol for in vitro cyst formation was recently published by Sharma et al. (2019). In other examples, the genetically modified mammalian cells are derived from a cell line. In some examples the cell line is pluripotent stem cell line (e.g., hiPSCs or hESCs) or a human kidney cell line. In some examples, the genetically modified mammalian cells are derived from HEK293, HK-2 or WT9-7 cell lines. In some preferred examples, the genetically modified mammalian cells express Polycystin 1 endogenously. In some embodiments genetically modified human cells are provided in a kidney organoid, e.g., a kidney organoid derived by differentiation of human pluripotent or human adult stem cells as reviewed in, e.g., Kang (2023), *Development & Reproduction*, 27(2):57-65.

The genetically modified cells disclosed herein can be genetically modified by any of a number of methods and strategies known in the art, e.g., transient transfection, stable transfection, and viral transduction. In some examples transfection with ASOs or non-viral vectors is carried out by nucleofection. In other examples transfection of cells is by lipofection.

Pharmaceutical Compositions

Also provided herein are pharmaceutical compositions comprising any of the foregoing ASOs, non-viral expression vectors, modified messenger RNAs (mmRNAs), and viral expression vectors disclosed herein, and formulated with at least a pharmaceutically acceptable excipient, including a carrier, filler, preservative, adjuvant, solubilizer and/or diluent.

Pharmaceutical compositions containing any of the ASOs or expression vector compositions described herein, for use in the methods disclosed herein, can be prepared according to conventional techniques well known in the pharmaceutical industry and described in the published literature. In some examples, a pharmaceutical composition for treating a subject comprises a therapeutically effective amount of any ASO or expression vector disclosed herein.

Pharmaceutically acceptable salts are suitable for use in contact with the tissues of humans and lower animals without undue toxicity, irritation, allergic response, etc., and are commensurate with a reasonable benefit/risk ratio. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In some examples, pharmaceutical compositions are formulated into any of a number of possible dosage forms including, but not limited to, topical ointments, solutions for intravenous administration, subcutaneous injection, intrathecal administration, intracisterna magna administration, tablets, capsules, gel capsules, liquid syrups, and soft gels. In some examples, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In some examples, a pharmaceutical formulation disclosed herein is provided in a form including, but not limited to, a solution, emulsion, microemulsion, foam or liposome-containing formulation (e.g., cationic or noncationic liposomes).

In some examples, pharmaceutical formulations comprising any of the ASOs or expression vectors described herein may comprise one or more penetration enhancers, carriers, excipients or other active or inactive ingredients as appropriate and known to the skilled person. In some examples, where a pharmaceutical composition includes liposomes, such liposomes can also include sterically stabilized liposomes, e.g., liposomes comprising one or more specialized lipids. These specialized lipids result in liposomes with enhanced circulation lifetimes. In some examples, a sterically stabilized liposome comprises one or more glycolipids or is derivatized with one or more hydrophilic polymers, such as PEG moiety. In some examples, a surfactant is included in the pharmaceutical formulation.

In some examples, a pharmaceutical composition also includes a penetration enhancer to enhance the delivery of ASOs or non-viral expression vectors, e.g., to aid diffusion across cell membranes and/or enhance the permeability of a lipophilic drug. In some examples, the penetration enhancers include a surfactant, a fatty acid, a bile salt, or a chelating agent.

In some examples, a pharmaceutical composition comprises a dose of ASOs or non-viral vectors ranging from about 0.0001 mg/kg to about 80 mg/kg, e.g., 0.005 mg/kg, 0.007 mg/kg, 0.01 mg/kg, 0.02 mg/kg, 0.03 mg/kg, 0.05 mg/kg, 0.1 mg/kg, 0.2 mg/kg, 0.5 mg/kg, 1 mg/kg, 3 mg/kg, 5 mg/kg, 8 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 77 mg/kg, or another dose ranging from about 0.01 mg/kg to about 80 mg/kg.

In some examples, a pharmaceutical composition comprises multiple ASOs or AR expression vectors. In some examples, a pharmaceutical composition comprises, in addition to ASOs or AR expression vectors, another drug or therapeutic agent suitable for treatment of a subject suffering from a condition associated with inflammation.

Methods

As described herein, ADPKD is associated with insufficient levels of functional Polycystin 1. Accordingly, the methods described herein include a method treating ADPKD by administering to the subject a therapeutically effective amount of a pharmaceutical composition comprising any of the ASOs or expression vectors disclosed herein. Likewise, in some examples, any of the ASOs or AR expression vectors disclosed herein are used in the manufacture of a medicament for reducing inflammation.

Also provided herein is a method for increasing the level of PKD1 mRNA and subsequently Polycystin 1 protein in a cell, ex vivo or in a tissue in vivo, the method comprising contacting the cell with an ASO, AR expression vector, or pharmaceutical composition, as disclosed herein, whereby cellular abnormalities associated with ADPKD, e.g., cyst formation are reduced.

In some examples, administration to a subject or contact with cells with any of the ASOs, AR expression vectors, or pharmaceutical compositions disclosed herein increases the level of PKD1 mRNA or Polycystin 1 protein about 1.1 to about 3-fold, e.g., 1.3 to about 2.7-fold, about 1.4 to about 2.6-fold, about 1.5 to about 2.5-fold, about 1.6 to about 2.4-fold, about 1.7 to about 2.3-fold, about 1.8 to about 2.2-fold, or another increased level of PKD1 mRNA or Polycystin 1 protein about 1.1 to about 3-fold compared to the level in the tissue without the administration or contact.

Suitable routes of administration for treatment with the compositions, pharmaceutical compositions, or medicaments disclosed herein include, but are not limited to, intravenous, intra-arterial, subcutaneous, intrathecal, oral and topical.

In some examples any of the treatment methods disclosed herein can, optionally, include the step of determining a level PKD1 mRNA, Polycystin 1 protein in the subject before and/or following the treatment.

As the skilled person will understand, the treatment methods disclosed herein include administration of the compositions and pharmaceutical compositions disclosed herein in a therapeutically effective amount to a subject (e.g., a human subject). The terms "effective amount" or "therapeutically effective amount," as used herein, refer to a sufficient amount of a disclosed ASO, non-viral or viral expression vector being administered to relieve to some extent one or more of the symptoms and/or clinical indicia associated with pathological inflammation in a particular disease or health condition. In some examples, an "effective amount" for therapeutic uses is the amount of one of the foregoing agents required to provide a clinically significant decrease in disease symptoms and/or inflammatory markers or to prevent disease symptoms without undue adverse side effects. An appropriate "effective amount" in any individual case may be determined using techniques, such as a dose escalation study. The term "therapeutically effective amount" includes, for example, a prophylactically effective amount. It is understood that "an effective amount" or "a therapeutically effective amount" can vary from subject to subject, due to variation in metabolism of the compound of any age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial. Where more than one therapeutic agent is used in combination, a "therapeutically effective amount" of each therapeutic agent can refer to an amount of the therapeutic agent that would be therapeutically effective when used on its own or may refer to a reduced amount that is therapeutically effective by virtue of its combination with one or more additional therapeutic agents.

Combination Treatments

The pharmaceutical compositions comprising any of the ASOs or AR expression vectors, disclosed herein, can also be used in combination with other agents of therapeutic value in the treatment of a condition associated with pathological inflammation. In general, other agents do not necessarily have to be administered in the same pharmaceutical composition, and may, because of different physical and chemical characteristics, preferably be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Compositions and pharmaceutical compositions comprising ASOs and/or expression vectors, and an additional therapeutic agent may be administered concurrently (e.g., simultaneously, essentially simultaneously or within the same treatment protocol) or sequentially, depending upon the stage and progression of the inflammatory disease to be treated, the condition of the patient, and the choice of specific therapeutic agents used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies, dosages of co-administered therapeutic agents will of course vary depending on the type of co-agents employed, ASO or expression vector, and the disease stage of the patient to be treated.

Pharmaceutical compositions comprising ASOs, AR or expression vectors, and an additional therapeutic agent that make up a combination therapy disclosed herein may be a combined dosage form or in separate dosage forms intended for substantially simultaneous administration. The pharmaceutical compositions that make up the combination therapy may also be administered sequentially, with either therapeutic agent being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of various physiological parameters may also be evaluated to determine the optimal dose interval.

Examples of suitable therapeutic agents for co-administration with a composition or a pharmaceutical composition disclosed herein include, but are not limited to, vasopressin V2 receptor antagonists (e.g., Tolvaptan), Angiotensin-converting enzyme (ACE) inhibitors, angiotensin-2 receptor blockers, paracetamol, opioids and antibiotics.

EXAMPLES

Example 1: Identification and Sequence Selection of PKD1 3' UTR Target Sequence Mutations in PKD1 lead to dysregulation and/or insufficient levels of functional Polycystin 1 associated with ADPKD onset and severity. miRNAs from the miR-17 family (e.g., miR-17-5p, miR-106a-5p, miR-106b-5p, miR-20a-5p, miR-93-5p) and the miR-200 family (e.g., miR-200b, miR200c, or miR-429) are known to bind to the 3' UTR of the PKD1 mRNA leading to a decrease in Polycystin 1 protein.

For a 3' UTR upregulation strategy, PMOs (SEQ ID NOs:2-351 or 353-362) are designed as part of a microwalk strategy to span the entire PKD13' UTR (SEQ ID NO:1) encompassing binding sites for miR-17 family (e.g., miR-17-5p, miR-106a-5p, miR-106b-5p, miR-20a-5p, miR-93-5p) and miR-200 family (e.g., miR-200b, miR200c, or miR-429) miRNAs. PMOs having sequences corresponding to SEQ ID NOs:47, 334, and 335 are complementary to the binding site for miR-17 family miRNAs (FIG. 1i), and PMOs having sequences corresponding to SEQ ID NOs:14, 73, 75, 336 and 337 are complementary to the binding sites for miR-200 family miRNAs (FIG. 1C). The miRNA binding sites are highlighted in bold (FIGS. 1B and 1C).

Example 2: Screening of PPMOs that Target the miR-17 Binding Site in PKD1 in HEK293 Cells for the Ability to Increase PKD1 Transcript Expression PMOs with sequences corresponding to PKD1 H46 3UTR(+604+628) (SEQ ID NO:47), PKD1 H46A(+611+635) (SEQ ID NO:334), and PKD1 H46A(+615+639) (SEQ ID NO:335), were conjugated to a cell penetrating peptide (SEQ ID NO:352) to generate peptide-PMOs (PPMOs). HEK293 cells were treated with PPMOs or controls for 24 h before total RNA was extracted using MagMAX total RNA 96 extraction kit method. PKD1 gene expression was assessed by digital droplet PCR (TaqMan; probe catalog number Hs00947394_gl). PKD1 transcript expression was normalised to the housekeeper TATA-Binding Protein (TBP, TaqMan, probe catalog number Hs00427620_ml) and changes calculated as fold-change compared to untreated cells.

As shown in FIG. 2, PPMOs corresponding to SEQ ID NOs:47 (+604+628), 334 (+611+635), and 335 (+615+639) respectively induced a dose-dependent increase of PKD1 mRNA greater than 1.1-fold compared to untreated cells. A non-target control (GTC CTR), predicted not to hybridize to human transcripts, was included as a sham treatment.

Example 3: Effect on PC1 Protein Levels, in an ADPKD Patient Cell Line, of PPMOs that Mask the Sequence in the 3' UTR of PKD1 Targeted by the miR-17 miRNA Seed Sequence PPMOs that demonstrated significant PKD1 mRNA upregulation, as per Example 2, were selected for their ability to upregulate Polycystin 1 (PC1) protein in an ADPKD patient cell line. The ADPKD patient cell line was established by immortalizing cells from a single proximal cortical tubule cyst taken from a patient with ADPKD, carrying the PKD1 heterozygous mutation (p.Q2556*). PPMOs were dissolved in molecular grade H2O to generate 1 mM stock solutions. Stock solutions were diluted in media and dosed at 10 μM with n=3 technical replicates per treatment condition. Untreated cells were treated with equivalent volume of media only. The cells were incubated for 5 days before the presence of Polycystin 1 (PC1) protein on the cell surface was measured via flow cytometry. The cells were incubated with an anti-rabbit Polycystin 1 antibody (ab74115, Abcam) followed by a goat anti-mouse antibody conjugated to Alexa Fluor 488 (A-11001, ThermoFisher). Comparison of the median fluorescence intensity (MFI) of each sample to untreated cells (UT) identified PMOs that increased expression of Polycystin 1, as illustrated in FIG. 3. PPMOs corresponding to SEQ ID NOs:47 (+604+628), 334 (+611+635), and 335 (+615+639) respectively induced an increase of Polycystin 1 protein greater than 1.1-fold compared to untreated cells.

Example 4: Functional Validation of PPMOs in a Patient-Derived Primary Cell 3D Cyst Model PPMOs that demonstrated significant Polycystin 1 protein upregulation, as per Example 3, were selected for functional validation in a patient-derived 3D cyst model. The model utilizes cyst cells extracted from kidneys donated by ADPKD patients. When grown ex vivo, these cells spontaneously form cysts in a 3D matrix and can be used to assess the functional effect of drug treatments on cyst growth. Immediately after seeding, patient cells were co-exposed to treatment. PPMOs were dissolved in molecular grade H2O and dosed at 1 μM, 3 μM, 10 μM and 20 μM with n=4 technical replicates per treatment condition. Control cells were treated with equivalent volume of H20 only. After 7 days of exposure, cultures were fixed and stained for actin cytoskeleton and nuclei. Growth and swelling of cysts were visualized by high-content microscopy imaging and images are analyzed using Ominer® image analysis software. FIG. 4 shows representative images of the size of 3D patient cyst after treated with 20 μM PPMO with sequences corresponding to SEQ ID NOs:47 (+604+628), 334 (+611+635), and 335 (+615+639).

Example 5: Quantification of Patient-Derived 3D Cyst Area and Cell Death to Determine the Therapeutic Index All images from the assay described in Example 4 were further analysed to determine the dose-dependent change of cyst area ($\mu \cdot m^2$) and cell death (%) for PPMOs with sequences corresponding to SEQ ID NOs:47 (+604+628), 334 (+611+635), and 335 (+615+639). See FIG. 5.

The PPMO corresponding to SEQ ID NO:47 (+604+628) showed efficacy in inhibiting cyst growth in a dose dependent manner with no evidence of cytotoxicity at up to 20 μM (FIGS. 5A and 5D). The PPMO corresponding to SEQ ID NO: 334 (+611+635) effectively inhibited cyst growth, however slight cytotoxicity was observed at 20 μM treatment (FIGS. 5B and 5E). The PPMO corresponding to SEQ ID NO: 335 (+615+639) was found to be cytotoxic at 20 μM. However, the PPMO demonstrated moderate inhibition of cyst growth at 10 μM treatment in cyst models derived from ADPK patient (FIGS. 5C and 5F).

Example 6: Optimization of PMO Sequences to Enhance PKD1 Upregulation Via Inhibition of miR-17 Binding to the 3'UTR of PKD1 Transcripts PMOs (SEQ ID NOs:353-361) were designed to microwalk SEQ ID NO:47 with some modifications, e.g., length shortening and engineered-base mismatch. Microwalked PMOs were conjugated with a cell-penetrating peptide (SEQ ID NO:352) to generate PPMOs and tested for their efficacy in PKD1 upregulation in HEK293 cells. HEK293 cells were treated with PPMOs or controls for 24 hours. Subsequently, total RNA was extracted using the MagMAX Total RNA 96 Extraction Kit method. The expression of PKD1 transcript was assessed by digital droplet PCR (TaqMan; probe catalog number Hs00947394_1). PKD1 transcript expression was normalized to the housekeepers TATA-Binding Protein (TBP, TaqMan; probe catalog number Hs00427620_ml) and DexH-Box Helicase 57 (DHX57, ThermoFisher; Assay ID Hs00376574_ml), and changes were calculated as fold-change compared to untreated cells. The results in FIG. 6 demonstrated a slight PKD1 upregulation (1.1-fold) when treated with PPMOs (+604+626)MM16, (+604+628)MM16, (+604+626), (+604+623), (+604+628) and (+604+627).

Example 7: Screening of PPMOs to Enhance PKD1 Upregulation Via Inhibition of miR-200 Binding to the 3'UTR of PKD1 Transcripts PMOs with sequences corresponding to SEQ ID NOs:14, 73, 75, 336-337, were designed to target binding the 3' UTR of the PKD1 mRNA to prevent binding of miR-200. Designed PMOs were conjugated to a cell penetrating peptide (SEQ ID NO:352) to generate peptide-PMOs (PP-MOs) and tested for their efficacy in HEK293 cells. Following for 24 h of PPMO treatment, total RNA was extracted using the MagMAX total RNA 96 extraction kit method. PKD1 gene expression was assessed by digital droplet PCR (TaqMan; probe catalog number Hs00947394g1). PKD1 transcript expression was normalised to the housekeeper TATA-Binding Protein (TBP, TaqMan, probe catalog number Hs00427620 ml) and changes calculated as fold-change compared to untreated cells. As shown in FIG. 7, PPMOs corresponding to SEQ ID NOs:17 (+505+529), 73 (+515+539), 336 (+677+701), and 337 (+688+712) slightly increased the expression of PKD1 mRNA (1.1-fold) compared to untreated cells.

Example 8: PC1 Upregulation Assessment for PPMO-Mediated Inhibition of miR-17 Binding in HEK293 Cells PPMOs with the sequences corresponding to SEQ ID NOs:47 (+604+628) and 334 (+611+635) were incubated to HEK293 for 5 days. The upregulation level of PC1 was assessed using western blot assay. At day 5 post-treatment, protein was extracted using RIPA buffer supplemented with 2% protease inhibitor cocktail and 2× PhosSTOP. Protein lysates were cleared, total protein quantitated using BCA protein kit. Samples were run on NuPAGE 3-8% Tris Acetate protein gels. Protein was transferred to nitrocellulose membrane by wet transfer. The membrane was stained for total protein and mouse anti-PC1 (Santa-Cruz, cat no sc130554) primary antibody followed by anti-mouse (IRDye® 800CW preabsorbed) secondary antibody. Blots were imaged on an Odyssey Imager, quantitative analysis was performed using Image Studio Ver 5.5 software (as shown in FIG. 8). The raw fluorescence signal for PC1 was first normalized to the raw fluorescence signal of loading control (total protein) and then expressed as fold-change relative to UT. As shown in FIG. 9, both PPMOs (+604+628) and (+611+635) induced dose dependent increase in PC1 protein up to 1.64 fold compared to UT up to day 5. A non-targeting control, predicted not to hybridize to human transcripts, was included as a negative control.

Example 9: Time-Course and Dose-Range Analysis of PPMO in Inducing PC1 Protein in Cell Line Derived from an ADPKD Patient WT9-7 cell line harboring a PKD1 nonsense mutation (p.Q2556*) was incubated with a PPMO (+604+628) corresponding to SEQ ID NO:47 at concentrations of 30 μM, 60 μM, 90 μM and 120 μM and incubated for 2, 3 and 5 days. PC1 protein levels were assessed to evaluate the efficacy of the PPMO. Protein extraction was performed using RIPA buffer supplemented with 2% protease inhibitor cocktail and 2× PhosSTOP. Protein lysates were cleared, total protein quantitated using BCA protein kit. Samples were run on NuPAGE 3-8% Tris Acetate protein gels. Protein was transferred to nitrocellulose membrane by wet transfer. The membrane was stained for total protein and mouse anti-PC1 (Santa-Cruz, Cat No. sc130554) primary antibody followed by anti-mouse (IRDye® 800CW preabsorbed) secondary antibody. Blots were imaged on an Odyssey Imager, quantitative analysis was performed using Image Studio Ver 5.5 software. The raw fluorescence signal for PC1 was first normalized to the raw fluorescence signal of loading control (total protein) and then expressed as fold-change relative to UT. Western blot images demonstrated PC1 expression in FIG. 10. PPMO (+604+628)-SEQ ID NO:47 induced a dose-dependent increase in PC1 protein levels, up to 1.36-fold compared to UT. The maximum PC1 upregulation was observed on day 2 and appeared to plateau at 90 μM.

It will be appreciated by persons skilled in the art that numerous variations and/or modifications may be made to the invention as shown in the specific examples without departing from the spirit or scope of the invention as broadly described. The present examples are, therefore, to be considered in all respects as illustrative and not restrictive.

All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Any discussion of documents, acts, materials, devices, articles or the like that has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES de Carvalho Ribeiro et al., 2020, Stem Cells International.

Dugal-Tessier et al., (2021), *J Clin Med.,* 10(4):838.

Osafune et al., 2021, Clinical and Experimental Nephrology, 25(6):574-584.

Prakash et al., 2019, Nucleic Acids Research, 47(12):6029-6044.

Sharma et al., 2019, Methods Cell Biol.

APPENDIX 1

Sequences and SEQ ID NOS

SEQ ID NO: 1
Human PKD1 transcript 3' UTR (PKD-201 canonical transcript
ENST00000262304.9)
TCCTCCTTCCTGGCGGGGGTGGGCCGTGGAGTCGGAGTGGACACCGCTCAGTATT
ACTTTCTGCCGCTGTCAAGGCCGAGGGCCAGGCAGAATGGCTGCACGTAGGTTC
CCCAGAGAGCAGGCAGGGGCATCTGTCTGTCTGTGGGCTTCAGCACTTTAAAGA
GGCTGTGTGGCCAACCAGGACCCAGGGTCCCCTCCCCAGCTCCCTTGGGAAGGA
CACAGCAGTATTGGACGGTTTCTAGCCTCTGAGATGCTAATTTATTTCCCCGAGT
CCTCAGGTACAGCGGGCTGTGCCCGGCCCCACCCCCTGGGCAGATGTCCCCCACT
GCTAAGGCTGCTGGCTTCAGGGAGGGTTAGCCTGCACCGCCGCCACCCTGCCCCT
AAGTTATTACCTCTCCAGTTCCTACCGTACTCCCTGCACCGTCTCACTGTGTGTCT
CGTGTCAGTAATTTATATGGTGTTAAAATGTGTATATTTTTGTATGTCACTATTTT
CACTAGGGCTGAGGGGCCTGCGCCCAGAGCTGGCCTCCCCCAACACCTGCTGCG
CTTGGTAGGTGTGGTGGCGTTATGGCAGCCCGGCTGCTGCTTGGATGCGAGCTTG
GCCTTGGGCCGGTGCTGGGGGCACAGCTGTCTGCCAGGCACTCTCATCACCCCAG
AGGCCTTGTCATCCTCCCTTGCCCCAGGCCAGGTAGCAAGAGAGCAGCGCCCAG
GCCTGCTGGCATCAGGTCTGGGCAAGTAGCAGGACTAGGCATGTCAGAGGACCC
CAGGGTGGTTAGAGGAAAAGACTCCTCCTGGGGGCTGGCTCCCAGGGTGGAGGA
AGGTGACTGTGTGTGTGTGTGTGTGCGCGCGCGCACGCGCGAGTGTGCTGTATGG
CCCAGGCAGCCTCAAGGCCCTCGGAGCTGGCTGTGCCTGCTTCTGTGTACCACTT
CTGTGGGCATGGCCGCTTCTAGAGCCTCGACACCCCCCCAACCCCCGCACCAAGC
AGACAAAGTCAATAAAAGAGCTGTCTGACTGCAA

TABLE 1

Exemplary ASO or AR Sequences Targeting PKD1 3☐ UTR Sequences

| SEQ ID NO | ASO_Seq | ASO_Name |
|---|---|---|
| 2 | GGCCCACCCCCGCCAGGAAGGAGGA | PKD1 H46 3UTR(+469+493) |
| 3 | CACGGCCCACCCCCGCCAGGAAGGA | PKD1 H46 3UTR(+472+496) |
| 4 | CTCCACGGCCCACCCCCGCCAGGAA | PKD1 H46 3UTR(+475+499) |
| 5 | CGACTCCACGGCCCACCCCCGCCAG | PKD1 H46 3UTR(+478+502) |
| 6 | CTCCGACTCCACGGCCCACCCCCGC | PKD1 H46 3UTR(+481+505) |
| 7 | CCACTCCGACTCCACGGCCCACCCC | PKD1 H46 3UTR(+484+508) |
| 8 | TGTCCACTCCGACTCCACGGCCCAC | PKD1 H46 3UTR(+487+511) |
| 9 | CGGTGTCCACTCCGACTCCACGGCC | PKD1 H46 3UTR(+490+514) |
| 10 | GAGCGGTGTCCACTCCGACTCCACG | PKD1 H46 3UTR(+493+517) |
| 11 | ACTGAGCGGTGTCCACTCCGACTCC | PKD1 H46 3UTR(+496+520) |
| 12 | AATACTGAGCGGTGTCCACTCCGAC | PKD1 H46 3UTR(+499+523) |
| 13 | AGTAATACTGAGCGGTGTCCACTCC | PKD1 H46 3UTR(+502+526) |
| 14 | GAAAGTAATACTGAGCGGTGTCCAC | PKD1 H46 3UTR(+505+529) |
| 15 | GCAGAAAGTAATACTGAGCGGTGTC | PKD1 H46 3UTR(+508+532) |

TABLE 1-continued

Exemplary ASO or AR Sequences Targeting
PKD1 3□ UTR Sequences

| SEQ ID NO | ASO_Seq | ASO_Name |
|---|---|---|
| 16 | GCGGCAGAAAGTAATACTGAGCGGT | PKD1 H46 3UTR(+511+535) |
| 17 | ACAGCGGCAGAAAGTAATACTGAGC | PKD1 H46 3UTR(+514+538) |
| 18 | TTGACAGCGGCAGAAAGTAATACTG | PKD1 H46 3UTR(+517+541) |
| 19 | GCCTTGACAGCGGCAGAAAGTAATA | PKD1 H46 3UTR(+520+544) |
| 20 | TCGGCCTTGACAGCGGCAGAAAGTA | PKD1 H46 3UTR(+523+547) |
| 21 | CCCTCGGCCTTGACAGCGGCAGAAA | PKD1 H46 3UTR(+526+550) |
| 22 | TGGCCCTCGGCCTTGACAGCGGCAG | PKD1 H46 3UTR(+529+553) |
| 23 | GCCTGGCCCTCGGCCTTGACAGCGG | PKD1 H46 3UTR(+532+556) |
| 24 | TCTGCCTGGCCCTCGGCCTTGACAG | PKD1 H46 3UTR(+535+559) |
| 25 | CATTCTGCCTGGCCCTCGGCCTTGA | PKD1 H46 3UTR(+538+562) |
| 26 | AGCCATTCTGCCTGGCCCTCGGCCT | PKD1 H46 3UTR(+541+565) |
| 27 | TGCAGCCATTCTGCCTGGCCCTCGG | PKD1 H46 3UTR(+544+568) |
| 28 | ACGTGCAGCCATTCTGCCTGGCCCT | PKD1 H46 3UTR(+547+571) |
| 29 | CCTACGTGCAGCCATTCTGCCTGGC | PKD1 H46 3UTR(+550+574) |
| 30 | GAACCTACGTGCAGCCATTCTGCCT | PKD1 H46 3UTR(+553+577) |
| 31 | GGGGAACCTACGTGCAGCCATTCTG | PKD1 H46 3UTR(+556+580) |
| 32 | TCTGGGGAACCTACGTGCAGCCATT | PKD1 H46 3UTR(+559+583) |
| 33 | CTCTCTGGGGAACCTACGTGCAGCC | PKD1 H46 3UTR(+562+586) |
| 34 | CTGCTCTCTGGGGAACCTACGTGCA | PKD1 H46 3UTR(+565+589) |
| 35 | TGCCTGCTCTCTGGGGAACCTACGT | PKD1 H46 3UTR(+568+592) |
| 36 | CCCTGCCTGCTCTCTGGGGAACCTA | PKD1 H46 3UTR(+571+595) |
| 37 | TGCCCCTGCCTGCTCTCTGGGGAAC | PKD1 H46 3UTR(+574+598) |
| 38 | AGATGCCCCTGCCTGCTCTCTGGGG | PKD1 H46 3UTR(+577+601) |
| 39 | GACAGATGCCCCTGCCTGCTCTCTG | PKD1 H46 3UTR(+580+604) |
| 40 | ACAGACAGATGCCCCTGCCTGCTCT | PKD1 H46 3UTR(+583+607) |
| 41 | CAGACAGACAGATGCCCCTGCCTGC | PKD1 H46 3UTR(+586+610) |
| 42 | CCACAGACAGACAGATGCCCCTGCC | PKD1 H46 3UTR(+589+613) |
| 43 | AGCCCACAGACAGACAGATGCCCCT | PKD1 H46 3UTR(+592+616) |
| 44 | TGAAGCCCACAGACAGACAGATGCC | PKD1 H46 3UTR(+595+619) |
| 45 | TGCTGAAGCCCACAGACAGACAGAT | PKD1 H46 3UTR(+598+622) |
| 46 | AAGTGCTGAAGCCCACAGACAGACA | PKD1 H46 3UTR(+601+625) |
| 47 | TTAAAGTGCTGAAGCCCACAGACAG | PKD1 H46 3UTR(+604+628) |
| 48 | TCTTTAAAGTGCTGAAGCCCACAGA | PKD1 H46 3UTR(+607+631) |
| 49 | GCCTCTTTAAAGTGCTGAAGCCCAC | PKD1 H46 3UTR(+610+634) |
| 50 | ACAGCCTCTTTAAAGTGCTGAAGCC | PKD1 H46 3UTR(+613+637) |
| 51 | CACACAGCCTCTTTAAAGTGCTGAA | PKD1 H46 3UTR(+616+640) |
| 52 | GGCCACACAGCCTCTTTAAAGTGCT | PKD1 H46 3UTR(+619+643) |

TABLE 1-continued

Exemplary ASO or AR Sequences Targeting
PKD1 3☐ UTR Sequences

| SEQ ID NO | ASO_Seq | ASO_Name |
|---|---|---|
| 53 | GTTGGCCACACAGCCTCTTTAAAGT | PKD1 H46 3UTR(+622+646) |
| 54 | CTGGTTGGCCACACAGCCTCTTTAA | PKD1 H46 3UTR(+625+649) |
| 55 | GTCCTGGTTGGCCACACAGCCTCTT | PKD1 H46 3UTR(+628+652) |
| 56 | TGGGTCCTGGTTGGCCACACAGCCT | PKD1 H46 3UTR(+631+655) |
| 57 | CCCTGGGTCCTGGTTGGCCACACAG | PKD1 H46 3UTR(+634+658) |
| 58 | GGACCCTGGGTCCTGGTTGGCCACA | PKD1 H46 3UTR(+637+661) |
| 59 | AGGGGACCCTGGGTCCTGGTTGGCC | PKD1 H46 3UTR(+640+664) |
| 60 | GGGAGGGGACCCTGGGTCCTGGTTG | PKD1 H46 3UTR(+643+667) |
| 61 | CTGGGGAGGGGACCCTGGGTCCTGG | PKD1 H46 3UTR(+646+670) |
| 62 | GAGCTGGGGAGGGGACCCTGGGTCC | PKD1 H46 3UTR(+649+673) |
| 63 | AGGGAGCTGGGGAGGGGACCCTGGG | PKD1 H46 3UTR(+652+676) |
| 64 | CCAAGGGAGCTGGGGAGGGGACCCT | PKD1 H46 3UTR(+655+679) |
| 65 | TTCCCAAGGGAGCTGGGGAGGGGAC | PKD1 H46 3UTR(+658+682) |
| 66 | TCCTTCCCAAGGGAGCTGGGGAGGG | PKD1 H46 3UTR(+661+685) |
| 67 | GTGTCCTTCCCAAGGGAGCTGGGGA | PKD1 H46 3UTR(+664+688) |
| 68 | GCTGTGTCCTTCCCAAGGGAGCTGG | PKD1 H46 3UTR(+667+691) |
| 69 | ACTGCTGTGTCCTTCCCAAGGGAGC | PKD1 H46 3UTR(+670+694) |
| 70 | AATACTGCTGTGTCCTTCCCAAGGG | PKD1 H46 3UTR(+673+697) |
| 71 | TCCAATACTGCTGTGTCCTTCCCAA | PKD1 H46 3UTR(+676+700) |
| 72 | CCGTCCAATACTGCTGTGTCCTTCC | PKD1 H46 3UTR(+679+703) |
| 73 | AAACCGTCCAATACTGCTGTGTCCT | PKD1 H46 3UTR(+682+706) |
| 74 | TAGAAACCGTCCAATACTGCTGTGT | PKD1 H46 3UTR(+685+709) |
| 75 | GGCTAGAAACCGTCCAATACTGCTG | PKD1 H46 3UTR(+688+712) |
| 76 | AGAGGCTAGAAACCGTCCAATACTG | PKD1 H46 3UTR(+691+715) |
| 77 | CTCAGAGGCTAGAAACCGTCCAATA | PKD1 H46 3UTR(+694+718) |
| 78 | CATCTCAGAGGCTAGAAACCGTCCA | PKD1 H46 3UTR(+697+721) |
| 79 | TAGCATCTCAGAGGCTAGAAACCGT | PKD1 H46 3UTR(+700+724) |
| 80 | AATTAGCATCTCAGAGGCTAGAAAC | PKD1 H46 3UTR(+703+727) |
| 81 | ATAAATTAGCATCTCAGAGGCTAGA | PKD1 H46 3UTR(+706+730) |
| 82 | GAAATAAATTAGCATCTCAGAGGCT | PKD1 H46 3UTR(+709+733) |
| 83 | GGGGAAATAAATTAGCATCTCAGAG | PKD1 H46 3UTR(+712+736) |
| 84 | CTCGGGGAAATAAATTAGCATCTCA | PKD1 H46 3UTR(+715+739) |
| 85 | GGACTCGGGGAAATAAATTAGCATC | PKD1 H46 3UTR(+718+742) |
| 86 | TGAGGACTCGGGGAAATAAATTAGC | PKD1 H46 3UTR(+721+745) |
| 87 | ACCTGAGGACTCGGGGAAATAAATT | PKD1 H46 3UTR(+724+748) |
| 88 | TGTACCTGAGGACTCGGGGAAATAA | PKD1 H46 3UTR(+727+751) |

TABLE 1-continued

Exemplary ASO or AR Sequences Targeting
PKD1 3□ UTR Sequences

| SEQ ID NO | ASO_Seq | ASO_Name |
|---|---|---|
| 89 | CGCTGTACCTGAGGACTCGGGGAAA | PKD1 H46 3UTR(+730+754) |
| 90 | GCCCGCTGTACCTGAGGACTCGGGG | PKD1 H46 3UTR(+733+757) |
| 91 | ACAGCCCGCTGTACCTGAGGACTCG | PKD1 H46 3UTR(+736+760) |
| 92 | GGCACAGCCCGCTGTACCTGAGGAC | PKD1 H46 3UTR(+739+763) |
| 93 | CCGGGCACAGCCCGCTGTACCTGAG | PKD1 H46 3UTR(+742+766) |
| 94 | GGGCCGGGCACAGCCCGCTGTACCT | PKD1 H46 3UTR(+745+769) |
| 95 | GTGGGGCCGGGCACAGCCCGCTGTA | PKD1 H46 3UTR(+748+772) |
| 96 | GGGGTGGGGCCGGGCACAGCCCGCT | PKD1 H46 3UTR(+751+775) |
| 97 | CAGGGGGTGGGGCCGGGCACAGCCC | PKD1 H46 3UTR(+754+778) |
| 98 | GCCCAGGGGGTGGGGCCGGGCACAG | PKD1 H46 3UTR(+757+781) |
| 99 | TCTGCCCAGGGGGTGGGGCCGGGCA | PKD1 H46 3UTR(+760+784) |
| 100 | ACATCTGCCCAGGGGGTGGGGCCGG | PKD1 H46 3UTR(+763+787) |
| 101 | GGGACATCTGCCCAGGGGGTGGGGC | PKD1 H46 3UTR(+766+790) |
| 102 | TGGGGACATCTGCCCAGGGGGTGG | PKD1 H46 3UTR(+769+793) |
| 103 | CAGTGGGGGACATCTGCCCAGGGGG | PKD1 H46 3UTR(+772+796) |
| 104 | TAGCAGTGGGGGACATCTGCCCAGG | PKD1 H46 3UTR(+775+799) |
| 105 | CCTTAGCAGTGGGGGACATCTGCCC | PKD1 H46 3UTR(+778+802) |
| 106 | CAGCCTTAGCAGTGGGGGACATCTG | PKD1 H46 3UTR(+781+805) |
| 107 | CAGCAGCCTTAGCAGTGGGGGACAT | PKD1 H46 3UTR(+784+808) |
| 108 | AGCCAGCAGCCTTAGCAGTGGGGGA | PKD1 H46 3UTR(+787+811) |
| 109 | TGAAGCCAGCAGCCTTAGCAGTGGG | PKD1 H46 3UTR(+790+814) |
| 110 | CCCTGAAGCCAGCAGCCTTAGCAGT | PKD1 H46 3UTR(+793+817) |
| 111 | CCTCCCTGAAGCCAGCAGCCTTAGC | PKD1 H46 3UTR(+796+820) |
| 112 | AACCCTCCCTGAAGCCAGCAGCCTT | PKD1 H46 3UTR(+799+823) |
| 113 | GCTAACCCTCCCTGAAGCCAGCAGC | PKD1 H46 3UTR(+802+826) |
| 114 | CAGGCTAACCCTCCCTGAAGCCAGC | PKD1 H46 3UTR(+805+829) |
| 115 | GTGCAGGCTAACCCTCCCTGAAGCC | PKD1 H46 3UTR(+808+832) |
| 116 | GCGGTGCAGGCTAACCCTCCCTGAA | PKD1 H46 3UTR(+811+835) |
| 117 | GCGGCGGTGCAGGCTAACCCTCCCT | PKD1 H46 3UTR(+814+838) |
| 118 | GTGGCGGCGGTGCAGGCTAACCCTC | PKD1 H46 3UTR(+817+841) |
| 119 | AGGGTGGCGGCGGTGCAGGCTAACC | PKD1 H46 3UTR(+820+844) |
| 120 | GGCAGGGTGGCGGCGGTGCAGGCTA | PKD1 H46 3UTR(+823+847) |
| 121 | AGGGGCAGGGTGGCGGCGGTGCAGG | PKD1 H46 3UTR(+826+850) |
| 122 | CTTAGGGGCAGGGTGGCGGCGGTGC | PKD1 H46 3UTR(+829+853) |
| 123 | TAACTTAGGGGCAGGGTGGCGGCGG | PKD1 H46 3UTR(+832+856) |
| 124 | TAATAACTTAGGGGCAGGGTGGCGG | PKD1 H46 3UTR(+835+859) |
| 125 | AGGTAATAACTTAGGGGCAGGGTGG | PKD1 H46 3UTR(+838+862) |

TABLE 1-continued

| | Exemplary ASO or AR Sequences Targeting PKD1 3☐ UTR Sequences | |
|---|---|---|
| SEQ ID NO | ASO_Seq | ASO_Name |
| 126 | GAGAGGTAATAACTTAGGGGCAGGG | PKD1 H46 3UTR(+841+865) |
| 127 | CTGGAGAGGTAATAACTTAGGGGCA | PKD1 H46 3UTR(+844+868) |
| 128 | GAACTGGAGAGGTAATAACTTAGGG | PKD1 H46 3UTR(+847+871) |
| 129 | TAGGAACTGGAGAGGTAATAACTTA | PKD1 H46 3UTR(+850+874) |
| 130 | CGGTAGGAACTGGAGAGGTAATAAC | PKD1 H46 3UTR(+853+877) |
| 131 | GTACGGTAGGAACTGGAGAGGTAAT | PKD1 H46 3UTR(+856+880) |
| 132 | GGAGTACGGTAGGAACTGGAGAGGT | PKD1 H46 3UTR(+859+883) |
| 133 | CAGGGAGTACGGTAGGAACTGGAGA | PKD1 H46 3UTR(+862+886) |
| 134 | GTGCAGGGAGTACGGTAGGAACTGG | PKD1 H46 3UTR(+865+889) |
| 135 | ACGGTGCAGGGAGTACGGTAGGAAC | PKD1 H46 3UTR(+868+892) |
| 136 | GAGACGGTGCAGGGAGTACGGTAGG | PKD1 H46 3UTR(+871+895) |
| 137 | AGTGAGACGGTGCAGGGAGTACGGT | PKD1 H46 3UTR(+874+898) |
| 138 | CACAGTGAGACGGTGCAGGGAGTAC | PKD1 H46 3UTR(+877+901) |
| 139 | ACACACAGTGAGACGGTGCAGGGAG | PKD1 H46 3UTR(+880+904) |
| 140 | GAGACACACAGTGAGACGGTGCAGG | PKD1 H46 3UTR(+883+907) |
| 141 | CACGAGACACACAGTGAGACGGTGC | PKD1 H46 3UTR(+886+910) |
| 142 | TGACACGAGACACACAGTGAGACGG | PKD1 H46 3UTR(+889+913) |
| 143 | TACTGACACGAGACACACAGTGAGA | PKD1 H46 3UTR(+892+916) |
| 144 | AATTACTGACACGAGACACACAGTG | PKD1 H46 3UTR(+895+919) |
| 145 | ATAAATTACTGACACGAGACACACA | PKD1 H46 3UTR(+898+922) |
| 146 | CATATAAATTACTGACACGAGACAC | PKD1 H46 3UTR(+901+925) |
| 147 | CACCATATAAATTACTGACACGAGA | PKD1 H46 3UTR(+904+928) |
| 148 | TAACACCATATAAATTACTGACACG | PKD1 H46 3UTR(+907+931) |
| 149 | TTTTAACACCATATAAATTACTGAC | PKD1 H46 3UTR(+910+934) |
| 150 | ACATTTTAACACCATATAAATTACT | PKD1 H46 3UTR(+913+937) |
| 151 | TACACATTTTAACACCATATAAATT | PKD1 H46 3UTR(+916+940) |
| 152 | ATATACACATTTTAACACCATATAA | PKD1 H46 3UTR(+919+943) |
| 153 | AAAATATACACATTTTAACACCATA | PKD1 H46 3UTR(+922+946) |
| 154 | ACAAAAATATACACATTTTAACACC | PKD1 H46 3UTR(+925+949) |
| 155 | CATACAAAAATATACACATTTTAAC | PKD1 H46 3UTR(+928+952) |
| 156 | TGACATACAAAAATATACACATTTT | PKD1 H46 3UTR(+931+955) |
| 157 | TAGTGACATACAAAAATATACACAT | PKD1 H46 3UTR(+934+958) |
| 158 | AAATAGTGACATACAAAAATATACA | PKD1 H46 3UTR(+937+961) |
| 159 | TGAAAATAGTGACATACAAAAATAT | PKD1 H46 3UTR(+940+964) |
| 160 | TAGTGAAAATAGTGACATACAAAAA | PKD1 H46 3UTR(+943+967) |
| 161 | CCCTAGTGAAAATAGTGACATACAA | PKD1 H46 3UTR(+946+970) |

TABLE 1-continued

| | Exemplary ASO or AR Sequences Targeting PKD1 3☐ UTR Sequences | |
|---|---|---|
| SEQ ID NO | ASO_Seq | ASO_Name |
| 162 | CAGCCCTAGTGAAAATAGTGACATA | PKD1 H46 3UTR(+949+973) |
| 163 | CCTCAGCCCTAGTGAAAATAGTGAC | PKD1 H46 3UTR(+952+976) |
| 164 | GCCCCTCAGCCCTAGTGAAAATAGT | PKD1 H46 3UTR(+955+979) |
| 165 | CAGGCCCCTCAGCCCTAGTGAAAAT | PKD1 H46 3UTR(+958+982) |
| 166 | GCGCAGGCCCCTCAGCCCTAGTGAA | PKD1 H46 3UTR(+961+985) |
| 167 | TGGGCGCAGGCCCCTCAGCCCTAGT | PKD1 H46 3UTR(+964+988) |
| 168 | CTCTGGGCGCAGGCCCCTCAGCCCT | PKD1 H46 3UTR(+967+991) |
| 169 | CAGCTCTGGGCGCAGGCCCCTCAGC | PKD1 H46 3UTR(+970+994) |
| 170 | GGCCAGCTCTGGGCGCAGGCCCCTC | PKD1 H46 3UTR(+973+997) |
| 171 | GGAGGCCAGCTCTGGGCGCAGGCCC | PKD1 H46 3UTR(+976+1000) |
| 172 | GGGGGAGGCCAGCTCTGGGCGCAGG | PKD1 H46 3UTR(+979+1003) |
| 173 | GTTGGGGGAGGCCAGCTCTGGGCGC | PKD1 H46 3UTR(+982+1006) |
| 174 | GGTGTTGGGGGAGGCCAGCTCTGGG | PKD1 H46 3UTR(+985+1009) |
| 175 | GCAGGTGTTGGGGGAGGCCAGCTCT | PKD1 H46 3UTR(+988+1012) |
| 176 | GCAGCAGGTGTTGGGGGAGGCCAGC | PKD1 H46 3UTR(+991+1015) |
| 177 | AGCGCAGCAGGTGTTGGGGGAGGCC | PKD1 H46 3UTR(+994+1018) |
| 178 | CCAAGCGCAGCAGGTGTTGGGGGAG | PKD1 H46 3UTR(+997+1021) |
| 179 | CTACCAAGCGCAGCAGGTGTTGGGG | PKD1 H46 3UTR(+1000+1024) |
| 180 | CACCTACCAAGCGCAGCAGGTGTTG | PKD1 H46 3UTR(+1003+1027) |
| 181 | CCACACCTACCAAGCGCAGCAGGTG | PKD1 H46 3UTR(+1006+1030) |
| 182 | CCACCACACCTACCAAGCGCAGCAG | PKD1 H46 3UTR(+1009+1033) |
| 183 | ACGCCACCACACCTACCAAGCGCAG | PKD1 H46 3UTR(+1012+1036) |
| 184 | ATAACGCCACCACACCTACCAAGCG | PKD1 H46 3UTR(+1015+1039) |
| 185 | GCCATAACGCCACCACACCTACCAA | PKD1 H46 3UTR(+1018+1042) |
| 186 | GCTGCCATAACGCCACCACACCTAC | PKD1 H46 3UTR(+1021+1045) |
| 187 | CGGGCTGCCATAACGCCACCACACC | PKD1 H46 3UTR(+1024+1048) |
| 188 | AGCCGGGCTGCCATAACGCCACCAC | PKD1 H46 3UTR(+1027+1051) |
| 189 | AGCAGCCGGGCTGCCATAACGCCAC | PKD1 H46 3UTR(+1030+1054) |
| 190 | AGCAGCAGCCGGGCTGCCATAACGC | PKD1 H46 3UTR(+1033+1057) |
| 191 | CCAAGCAGCAGCCGGGCTGCCATAA | PKD1 H46 3UTR(+1036+1060) |
| 192 | CATCCAAGCAGCAGCCGGGCTGCCA | PKD1 H46 3UTR(+1039+1063) |
| 193 | TCGCATCCAAGCAGCAGCCGGGCTG | PKD1 H46 3UTR(+1042+1066) |
| 194 | AGCTCGCATCCAAGCAGCAGCCGGG | PKD1 H46 3UTR(+1045+1069) |
| 195 | CCAAGCTCGCATCCAAGCAGCAGCC | PKD1 H46 3UTR(+1048+1072) |
| 196 | AGGCCAAGCTCGCATCCAAGCAGCA | PKD1 H46 3UTR(+1051+1075) |
| 197 | CCAAGGCCAAGCTCGCATCCAAGCA | PKD1 H46 3UTR(+1054+1078) |
| 198 | GGCCCAAGGCCAAGCTCGCATCCAA | PKD1 H46 3UTR(+1057+1081) |

TABLE 1-continued

| | Exemplary ASO or AR Sequences Targeting PKD1 3□ UTR Sequences | |
|---|---|---|
| SEQ ID NO | ASO_Seq | ASO_Name |
| 199 | ACCGGCCCAAGGCCAAGCTCGCATC | PKD1 H46 3UTR(+1060+1084) |
| 200 | AGCACCGGCCCAAGGCCAAGCTCGC | PKD1 H46 3UTR(+1063+1087) |
| 201 | CCCAGCACCGGCCCAAGGCCAAGCT | PKD1 H46 3UTR(+1066+1090) |
| 202 | GCCCCCAGCACCGGCCCAAGGCCAA | PKD1 H46 3UTR(+1069+1093) |
| 203 | TGTGCCCCCAGCACCGGCCCAAGGC | PKD1 H46 3UTR(+1072+1096) |
| 204 | AGCTGTGCCCCCAGCACCGGCCCAA | PKD1 H46 3UTR(+1075+1099) |
| 205 | GACAGCTGTGCCCCCAGCACCGGCC | PKD1 H46 3UTR(+1078+1102) |
| 206 | GCAGACAGCTGTGCCCCCAGCACCG | PKD1 H46 3UTR(+1081+1105) |
| 207 | CTGGCAGACAGCTGTGCCCCCAGCA | PKD1 H46 3UTR(+1084+1108) |
| 208 | TGCCTGGCAGACAGCTGTGCCCCCA | PKD1 H46 3UTR(+1087+1111) |
| 209 | GAGTGCCTGGCAGACAGCTGTGCCC | PKD1 H46 3UTR(+1090+1114) |
| 210 | TGAGAGTGCCTGGCAGACAGCTGTG | PKD1 H46 3UTR(+1093+1117) |
| 211 | TGATGAGAGTGCCTGGCAGACAGCT | PKD1 H46 3UTR(+1096+1120) |
| 212 | GGGTGATGAGAGTGCCTGGCAGACA | PKD1 H46 3UTR(+1099+1123) |
| 213 | CTGGGGTGATGAGAGTGCCTGGCAG | PKD1 H46 3UTR(+1102+1126) |
| 214 | CCTCTGGGGTGATGAGAGTGCCTGG | PKD1 H46 3UTR(+1105+1129) |
| 215 | AGGCCTCTGGGGTGATGAGAGTGCC | PKD1 H46 3UTR(+1108+1132) |
| 216 | ACAAGGCCTCTGGGGTGATGAGAGT | PKD1 H46 3UTR(+1111+1135) |
| 217 | ATGACAAGGCCTCTGGGGTGATGAG | PKD1 H46 3UTR(+1114+1138) |
| 218 | AGGATGACAAGGCCTCTGGGGTGAT | PKD1 H46 3UTR(+1117+1141) |
| 219 | GGGAGGATGACAAGGCCTCTGGGGT | PKD1 H46 3UTR(+1120+1144) |
| 220 | CAAGGGAGGATGACAAGGCCTCTGG | PKD1 H46 3UTR(+1123+1147) |
| 221 | GGGCAAGGGAGGATGACAAGGCCTC | PKD1 H46 3UTR(+1126+1150) |
| 222 | CTGGGGCAAGGGAGGATGACAAGGC | PKD1 H46 3UTR(+1129+1153) |
| 223 | GGCCTGGGGCAAGGGAGGATGACAA | PKD1 H46 3UTR(+1132+1156) |
| 224 | CCTGGCCTGGGGCAAGGGAGGATGA | PKD1 H46 3UTR(+1135+1159) |
| 225 | CTACCTGGCCTGGGGCAAGGGAGGA | PKD1 H46 3UTR(+1138+1162) |
| 226 | TTGCTACCTGGCCTGGGGCAAGGGA | PKD1 H46 3UTR(+1141+1165) |
| 227 | CTCTTGCTACCTGGCCTGGGGCAAG | PKD1 H46 3UTR(+1144+1168) |
| 228 | GCTCTCTTGCTACCTGGCCTGGGGC | PKD1 H46 3UTR(+1147+1171) |
| 229 | GCTGCTCTCTTGCTACCTGGCCTGG | PKD1 H46 3UTR(+1150+1174) |
| 230 | GGCGCTGCTCTCTTGCTACCTGGCC | PKD1 H46 3UTR(+1153+1177) |
| 231 | CTGGGCGCTGCTCTCTTGCTACCTG | PKD1 H46 3UTR(+1156+1180) |
| 232 | GGCCTGGGCGCTGCTCTCTTGCTAC | PKD1 H46 3UTR(+1159+1183) |
| 233 | GCAGGCCTGGGCGCTGCTCTCTTGC | PKD1 H46 3UTR(+1162+1186) |
| 234 | CCAGCAGGCCTGGGCGCTGCTCTCT | PKD1 H46 3UTR(+1165+1189) |

TABLE 1-continued

Exemplary ASO or AR Sequences Targeting
PKD1 3☐ UTR Sequences

| SEQ ID NO | ASO_Seq | ASO_Name |
|---|---|---|
| 235 | ATGCCAGCAGGCCTGGGCGCTGCTC | PKD1 H46 3UTR(+1168+1192) |
| 236 | CTGATGCCAGCAGGCCTGGGCGCTG | PKD1 H46 3UTR(+1171+1195) |
| 237 | GACCTGATGCCAGCAGGCCTGGGCG | PKD1 H46 3UTR(+1174+1198) |
| 238 | CCAGACCTGATGCCAGCAGGCCTGG | PKD1 H46 3UTR(+1177+1201) |
| 239 | TGCCCAGACCTGATGCCAGCAGGCC | PKD1 H46 3UTR(+1180+1204) |
| 240 | ACTTGCCCAGACCTGATGCCAGCAG | PKD1 H46 3UTR(+1183+1207) |
| 241 | GCTACTTGCCCAGACCTGATGCCAG | PKD1 H46 3UTR(+1186+1210) |
| 242 | CCTGCTACTTGCCCAGACCTGATGC | PKD1 H46 3UTR(+1189+1213) |
| 243 | AGTCCTGCTACTTGCCCAGACCTGA | PKD1 H46 3UTR(+1192+1216) |
| 244 | CCTAGTCCTGCTACTTGCCCAGACC | PKD1 H46 3UTR(+1195+1219) |
| 245 | ATGCCTAGTCCTGCTACTTGCCCAG | PKD1 H46 3UTR(+1198+1222) |
| 246 | GACATGCCTAGTCCTGCTACTTGCC | PKD1 H46 3UTR(+1201+1225) |
| 247 | TCTGACATGCCTAGTCCTGCTACTT | PKD1 H46 3UTR(+1204+1228) |
| 248 | TCCTCTGACATGCCTAGTCCTGCTA | PKD1 H46 3UTR(+1207+1231) |
| 249 | GGGTCCTCTGACATGCCTAGTCCTG | PKD1 H46 3UTR(+1210+1234) |
| 250 | CTGGGGTCCTCTGACATGCCTAGTC | PKD1 H46 3UTR(+1213+1237) |
| 251 | ACCCTGGGGTCCTCTGACATGCCTA | PKD1 H46 3UTR(+1216+1240) |
| 252 | ACCACCCTGGGGTCCTCTGACATGC | PKD1 H46 3UTR(+1219+1243) |
| 253 | CTAACCACCCTGGGGTCCTCTGACA | PKD1 H46 3UTR(+1222+1246) |
| 254 | CCTCTAACCACCCTGGGGTCCTCTG | PKD1 H46 3UTR(+1225+1249) |
| 255 | TTTCCTCTAACCACCCTGGGGTCCT | PKD1 H46 3UTR(+1228+1252) |
| 256 | TCTTTTCCTCTAACCACCCTGGGGT | PKD1 H46 3UTR(+1231+1255) |
| 257 | GAGTCTTTTCCTCTAACCACCCTGG | PKD1 H46 3UTR(+1234+1258) |
| 258 | GAGGAGTCTTTTCCTCTAACCACCC | PKD1 H46 3UTR(+1237+1261) |
| 259 | CAGGAGGAGTCTTTTCCTCTAACCA | PKD1 H46 3UTR(+1240+1264) |
| 260 | CCCCAGGAGGAGTCTTTTCCTCTAA | PKD1 H46 3UTR(+1243+1267) |
| 261 | AGCCCCCAGGAGGAGTCTTTTCCTC | PKD1 H46 3UTR(+1246+1270) |
| 262 | GCCAGCCCCCAGGAGGAGTCTTTTC | PKD1 H46 3UTR(+1249+1273) |
| 263 | GGAGCCAGCCCCCAGGAGGAGTCTT | PKD1 H46 3UTR(+1252+1276) |
| 264 | CTGGGAGCCAGCCCCCAGGAGGAGT | PKD1 H46 3UTR(+1255+1279) |
| 265 | ACCCTGGGAGCCAGCCCCCAGGAGG | PKD1 H46 3UTR(+1258+1282) |
| 266 | TCCACCCTGGGAGCCAGCCCCCAGG | PKD1 H46 3UTR(+1261+1285) |
| 267 | TCCTCCACCCTGGGAGCCAGCCCCC | PKD1 H46 3UTR(+1264+1288) |
| 268 | CCTTCCTCCACCCTGGGAGCCAGCC | PKD1 H46 3UTR(+1267+1291) |
| 269 | TCACCTTCCTCCACCCTGGGAGCCA | PKD1 H46 3UTR(+1270+1294) |
| 270 | CAGTCACCTTCCTCCACCCTGGGAG | PKD1 H46 3UTR(+1273+1297) |
| 271 | ACACAGTCACCTTCCTCCACCCTGG | PKD1 H46 3UTR(+1276+1300) |

TABLE 1-continued

Exemplary ASO or AR Sequences Targeting
PKD1 3☐ UTR Sequences

| SEQ ID NO | ASO_Seq | ASO_Name |
|---|---|---|
| 272 | CACACACAGTCACCTTCCTCCACCC | PKD1 H46 3UTR(+1279+1303) |
| 273 | ACACACACACAGTCACCTTCCTCCA | PKD1 H46 3UTR(+1282+1306) |
| 274 | CACACACACACAGTCACCTTCCT | PKD1 H46 3UTR(+1285+1309) |
| 275 | ACACACACACACACAGTCACCTT | PKD1 H46 3UTR(+1288+1312) |
| 276 | CGCACACACACACACACAGTCAC | PKD1 H46 3UTR(+1291+1315) |
| 277 | GCGCGCACACACACACACACAGT | PKD1 H46 3UTR(+1294+1318) |
| 278 | CGCGCGCGCACACACACACACAC | PKD1 H46 3UTR(+1297+1321) |
| 279 | GTGCGCGCGCGCACACACACACA | PKD1 H46 3UTR(+1300+1324) |
| 280 | CGCGTGCGCGCGCGCACACACAC | PKD1 H46 3UTR(+1303+1327) |
| 281 | TCGCGCGTGCGCGCGCGCACACACA | PKD1 H46 3UTR(+1306+1330) |
| 282 | CACTCGCGCGTGCGCGCGCGCACAC | PKD1 H46 3UTR(+1309+1333) |
| 283 | GCACACTCGCGCGTGCGCGCGCGCA | PKD1 H46 3UTR(+1312+1336) |
| 284 | ACAGCACACTCGCGCGTGCGCGCGC | PKD1 H46 3UTR(+1315+1339) |
| 285 | CATACAGCACACTCGCGCGTGCGCG | PKD1 H46 3UTR(+1318+1342) |
| 286 | GGCCATACAGCACACTCGCGCGTGC | PKD1 H46 3UTR(+1321+1345) |
| 287 | CTGGGCCATACAGCACACTCGCGCG | PKD1 H46 3UTR(+1324+1348) |
| 288 | TGCCTGGGCCATACAGCACACTCGC | PKD1 H46 3UTR(+1327+1351) |
| 289 | GGCTGCCTGGGCCATACAGCACACT | PKD1 H46 3UTR(+1330+1354) |
| 290 | TGAGGCTGCCTGGGCCATACAGCAC | PKD1 H46 3UTR(+1333+1357) |
| 291 | CCTTGAGGCTGCCTGGGCCATACAG | PKD1 H46 3UTR(+1336+1360) |
| 292 | GGGCCTTGAGGCTGCCTGGGCCATA | PKD1 H46 3UTR(+1339+1363) |
| 293 | CGAGGGCCTTGAGGCTGCCTGGGCC | PKD1 H46 3UTR(+1342+1366) |
| 294 | CTCCGAGGGCCTTGAGGCTGCCTGG | PKD1 H46 3UTR(+1345+1369) |
| 295 | CAGCTCCGAGGGCCTTGAGGCTGCC | PKD1 H46 3UTR(+1348+1372) |
| 296 | AGCCAGCTCCGAGGGCCTTGAGGCT | PKD1 H46 3UTR(+1351+1375) |
| 297 | CACAGCCAGCTCCGAGGGCCTTGAG | PKD1 H46 3UTR(+1354+1378) |
| 298 | AGGCACAGCCAGCTCCGAGGGCCTT | PKD1 H46 3UTR(+1357+1381) |
| 299 | AGCAGGCACAGCCAGCTCCGAGGGC | PKD1 H46 3UTR(+1360+1384) |
| 300 | AGAAGCAGGCACAGCCAGCTCCGAG | PKD1 H46 3UTR(+1363+1387) |
| 301 | CACAGAAGCAGGCACAGCCAGCTCC | PKD1 H46 3UTR(+1366+1390) |
| 302 | GTACACAGAAGCAGGCACAGCCAGC | PKD1 H46 3UTR(+1369+1393) |
| 303 | GTGGTACACAGAAGCAGGCACAGCC | PKD1 H46 3UTR(+1372+1396) |
| 304 | GAAGTGGTACACAGAAGCAGGCACA | PKD1 H46 3UTR(+1375+1399) |
| 305 | ACAGAAGTGGTACACAGAAGCAGGC | PKD1 H46 3UTR(+1378+1402) |
| 306 | CCCACAGAAGTGGTACACAGAAGCA | PKD1 H46 3UTR(+1381+1405) |
| 307 | ATGCCCACAGAAGTGGTACACAGAA | PKD1 H46 3UTR(+1384+1408) |

TABLE 1-continued

Exemplary ASO or AR Sequences Targeting
PKD1 3☐ UTR Sequences

| SEQ ID NO | ASO_Seq | ASO_Name |
|---|---|---|
| 308 | GCCATGCCCACAGAAGTGGTACACA | PKD1 H46 3UTR(+1387+1411) |
| 309 | GCGGCCATGCCCACAGAAGTGGTAC | PKD1 H46 3UTR(+1390+1414) |
| 310 | GAAGCGGCCATGCCCACAGAAGTGG | PKD1 H46 3UTR(+1393+1417) |
| 311 | CTAGAAGCGGCCATGCCCACAGAAG | PKD1 H46 3UTR(+1396+1420) |
| 312 | GCTCTAGAAGCGGCCATGCCCACAG | PKD1 H46 3UTR(+1399+1423) |
| 313 | GAGGCTCTAGAAGCGGCCATGCCCA | PKD1 H46 3UTR(+1402+1426) |
| 314 | GTCGAGGCTCTAGAAGCGGCCATGC | PKD1 H46 3UTR(+1405+1429) |
| 315 | GGTGTCGAGGCTCTAGAAGCGGCCA | PKD1 H46 3UTR(+1408+1432) |
| 316 | GGGGGTGTCGAGGCTCTAGAAGCGG | PKD1 H46 3UTR(+1411+1435) |
| 317 | TGGGGGGGTGTCGAGGCTCTAGAAG | PKD1 H46 3UTR(+1414+1438) |
| 318 | GGTTGGGGGGGTGTCGAGGCTCTAG | PKD1 H46 3UTR(+1417+1441) |
| 319 | GGGGGTTGGGGGGGTGTCGAGGCTC | PKD1 H46 3UTR(+1420+1444) |
| 320 | TGCGGGGGTTGGGGGGGTGTCGAGG | PKD1 H46 3UTR(+1423+1447) |
| 321 | TGGTGCGGGGGTTGGGGGGGTGTCG | PKD1 H46 3UTR(+1426+1450) |
| 322 | GCTTGGTGCGGGGGTTGGGGGGGTG | PKD1 H46 3UTR(+1429+1453) |
| 323 | TCTGCTTGGTGCGGGGGTTGGGGGG | PKD1 H46 3UTR(+1432+1456) |
| 324 | TTGTCTGCTTGGTGCGGGGGTTGGG | PKD1 H46 3UTR(+1435+1459) |
| 325 | ACTTTGTCTGCTTGGTGCGGGGGTT | PKD1 H46 3UTR(+1438+1462) |
| 326 | TTGACTTTGTCTGCTTGGTGCGGGG | PKD1 H46 3UTR(+1441+1465) |
| 327 | TTATTGACTTTGTCTGCTTGGTGCG | PKD1 H46 3UTR(+1444+1468) |
| 328 | CTTTTATTGACTTTGTCTGCTTGGT | PKD1 H46 3UTR(+1447+1471) |
| 329 | GCTCTTTTATTGACTTTGTCTGCTT | PKD1 H46 3UTR(+1450+1474) |
| 330 | ACAGCTCTTTTATTGACTTTGTCTG | PKD1 H46 3UTR(+1453+1477) |
| 331 | CAGACAGCTCTTTTATTGACTTTGT | PKD1 H46 3UTR(+1456+1480) |
| 332 | AGTCAGACAGCTCTTTTATTGACTT | PKD1 H46 3UTR(+1459+1483) |
| 333 | TGCAGTCAGACAGCTCTTTTATTGA | PKD1 H46 3UTR(+1462+1486) |
| 334 | AGCCTCTTTAAAGTGCTGAAGCCCA | PKD1 H46 3UTR(+611+635) |
| 335 | ACACAGCCTCTTTAAAGTGCTGAAG | PKD1 H46 3UTR(+615+639) |
| 336 | GTCCAATACTGCTGTGTCCTTCCCA | PKD1 H46 3UTR(+677+701) |
| 337 | GACAGCGGCAGAAAGTAATACTGAG | PKD1 H46 3UTR(+515+539) |
| 338 | CTCTTTAAAGTGCTGAAGCCCACAG | PKD1 H46 3UTR(+608+632) |
| 339 | CAGCCTCTTTAAAGTGCTGAAGCCC | PKD1 H46 3UTR(+612+636) |
| 340 | CACAGCCTCTTTAAAGTGCTGAAGC | PKD1 H46 3UTR(+614+638) |
| 341 | TTAAAGTGCTGAAGCCCACATACAG | PKD1 H46 3UTR(+604+628)MM, G > T |
| 342 | TCTTTAAAGTGCTGAAGCCCACATA | PKD1 H46 3UTR(+607+631)MM, G > T |

TABLE 1-continued

| Exemplary ASO or AR Sequences Targeting PKD1 3☐ UTR Sequences | | |
|---|---|---|
| SEQ ID NO | ASO_Seq | ASO_Name |
| 343 | CTCTTTAAAGTGCTGAAGCACACAG | PKD1_H46 3UTR(+608+632)MM, C > A |
| 344 | GCCTCCTTAAAGTGCTGAAGCCCAC | PKD1_H46 3UTR(+610+634)MM, T > C |
| 345 | AGCCTCTATAAAGTGCTGAAGCCCA | PKD1_H46 3UTR(+611+635)MM, T > A |
| 346 | CAGCCTCTATAAAGTGCTGAAGCCC | PKD1_H46 3UTR(+612+636)MM, T > A |
| 347 | ACAGCCTCTTTAAAGTGCTGAATCC | PKD1_H46 3UTR(+613+637)MM, G > T |
| 348 | CACAGCCTCTTTAAAGTGCTGAATC | PKD1_H46 3UTR(+614+638)MM, G > T |
| 349 | ACACAACCTCTTTAAAGTGCTGAAG | PKD1_H46 3UTR(+615+639)MM, G > A |
| 350 | CACATAGCCTCTTTAAAGTGCTGAA | PKD1_H46 3UTR(+616+640)MM, C > T |
| 351 | GGCCACACAGTCTCTTTAAAGTGCT | PKD1_H46 3UTR(+619+643)MM, C > T |
| 353 | TTAAAGTGCTGAAGCCCAC | PKD1_H46 3UTR(+604+622) |
| 354 | TTAAAGTGCTGAAGCCCACAG | PKD1_H46 3UTR(+604+624) |
| 355 | TTAAAGTGCTGAAGCCCACAGAC | PKD1_H46 3UTR(+604+626) |
| 356 | TTAAAGTGCTGAAGCTCACAGAC | PKD1_H46 3UTR(+604+626)MM16 |
| 357 | TTAAAGTGCTGAAGCTCACAGACAG | PKD1_H46 3UTR(+604+628)MM16 |
| 358 | TTAAAGTGCTGAAGCCCACA | PKD1_H46 3UTR(+604+623) |
| 359 | TTAAAGTGCTGAAGCCCACAGA | PKD1_H46 3UTR(+604+625) |
| 360 | TTAAAGTGCTGAAGCCCACAGACA | PKD1_H46 3UTR(+604+627) |
| 361 | TTAAAGTACTGAAGCCCACAGACAG | PKD1_H46 3UTR(+604+628)MM8 |
| 362 | GTGCTGAAGCCCACAGACAGACAG | PKD1_H46 3UTR(+603+626) |

50

Amino acid sequence of CPP
SEQ ID NO: 352
RRSRTARAGRPGRNSSRPSAPR.

The invention claimed is:

1. An antisense oligonucleotide, wherein the nucleotide sequence of the antisense oligonucleotide consists of SEQ ID NO:47, wherein the antisense oligonucleotide is a phosphorodiamidate morpholino oligonucleotide.

2. A pharmaceutical composition comprising the antisense oligonucleotide according to claim 1, and a pharmaceutically acceptable excipient.

3. A method for treating autosomal dominant polycystic kidney disease (ADPKD) in a human subject in need thereof, wherein the ADPKD is caused by a mutation in a single copy of a Polycystin 1, Transient Receptor Potential Channel Interacting (PKD1) gene, wherein the subject also has an unmutated copy of the PKD1, the method comprising administering to the human subject a therapeutically effective amount of the pharmaceutical composition according to claim 2, wherein the antisense oligonucleotide binds to a targeted portion of the 3' untranslated region (UTR) of a mRNA encoded by the unmutated copy of the PKD1 gene that comprises in the 3'UTR a functional binding site for miR-17 family miRNAs, whereby binding of a miR-17 family member miRNA to the binding site is reduced.

4. The antisense oligonucleotide according to claim 1, wherein the antisense oligonucleotide further comprises a cell-penetrating peptide (CPP) covalently linked to the antisense oligonucleotide.

5. The antisense oligonucleotide according to claim 4, wherein the amino acid sequence of the CPP comprises SEQ ID NO:352.

6. The antisense oligonucleotide according to claim 5, wherein the amino acid sequence of the CPP consists of SEQ ID NO:352.

7. The antisense oligonucleotide according to claim 5, wherein any amino acid other than glycine is a D-amino acid.

8. The antisense oligonucleotide according to claim 4, wherein the CPP is linked to the 5' end of the antisense oligonucleotide.

9. A pharmaceutical composition comprising the antisense oligonucleotide according to claim 4, and a pharmaceutically acceptable excipient.

10. A method for treating ADPKD in a human subject in need thereof, wherein the ADPKD is caused by a mutation in a single copy of a PKD1 gene, wherein the subject also has an unmutated copy of the PKD1 gene, the method comprising administering to the human subject a therapeutically effective amount of the pharmaceutical composition according to claim 9, wherein the antisense oligonucleotide binds to a targeted portion of the 3' UTR of a mRNA encoded by the unmutated copy of the PKD1 gene that comprises in the 3'UTR a functional binding site for miR-17 family miRNAs, whereby binding of a miR-17 family member miRNA to the binding site is reduced.

\* \* \* \* \*

SEQUENCE LISTING

Sequence total quantity: 362
SEQ ID NO: 1          moltype = DNA   length = 1019
FEATURE               Location/Qualifiers
source                1..1019
                      mol_type = other DNA
                      organism = Homo sapiens
SEQUENCE: 1
tcctccttcc tggcgggggt gggccgtgga gtcggagtgg acaccgctca gtattacttt   60
ctgccgctgt caaggccgag ggccaggcag aatggctgca cgtaggttcc ccagagagca  120

-continued

```
ggcaggggca tctgtctgtc tgtgggcttc agcactttaa agaggctgtg tggccaacca    180
ggacccaggg tcccctcccc agctcccttg ggaaggacac agcagtattg gacggtttct    240
agcctctgag atgctaattt atttccccga gtcctcaggt acagcgggct gtgcccggcc    300
ccaccccctg ggcagatgtc ccccactgct aaggctgctg gcttcaggga gggttagcct    360
gcaccgccgc caccctgccc ctaagttatt acctctccag ttcctaccgt actccctgca    420
ccgtctcact gtgtgtctcg tgtcagtaat ttatatggtg ttaaaatgtg tatatttttg    480
tatgtcacta ttttcactag ggctgagggg cctgcgccca gagctggcct cccccaacac    540
ctgctgcgct tggtaggtgt ggtggcgtta tggcagcccg gctgctgctt ggatgcgagc    600
ttggccttgg gccggtgctg ggggcacagc tgtctgccag gcactctcat caccccagag    660
gccttgtcat cctcccttgc cccaggccag gtagcaagag agcagcgccc aggcctgctg    720
gcatcaggtc tgggcaagta gcaggactag gcatgtcaga ggaccccagg gtggttagag    780
gaaaagactc ctcctggggg ctggctccca gggtggagga aggtgactgt gtgtgtgtgt    840
gtgtgcgcgc gcgcacgcgc gagtgtgctg tatggcccag gcagcctcaa ggccctcgga    900
gctggctgtg cctgcttctg tgtaccactt ctgtgtgggcat ggccgcttct agagcctcga    960
cacccccccca accccgcac caagcagaca aagtcaataa aagagctgtc tgactgcaa   1019
```

SEQ ID NO: 2           moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 2
ggcccacccc cgccaggaag gagga                                           25

SEQ ID NO: 3           moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 3
cacggcccac ccccgccagg aagga                                           25

SEQ ID NO: 4           moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 4
ctccacggcc cacccccgcc aggaa                                           25

SEQ ID NO: 5           moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 5
cgactccacg gcccaccccc gccag                                           25

SEQ ID NO: 6           moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 6
ctccgactcc acggcccacc cccgc                                           25

SEQ ID NO: 7           moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 7
ccactccgac tccacggccc acccc                                           25

SEQ ID NO: 8           moltype = DNA   length = 25
FEATURE                Location/Qualifiers
misc_feature           1..25
```

-continued

```
                         note = Synthetic sequence
source                   1..25
                         mol_type = other DNA
                         organism = synthetic construct
SEQUENCE: 8
tgtccactcc gactccacgg cccac                                            25

SEQ ID NO: 9             moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 9
cggtgtccac tccgactcca cggcc                                            25

SEQ ID NO: 10            moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 10
gagcggtgtc cactccgact ccacg                                            25

SEQ ID NO: 11            moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 11
actgagcggt gtccactccg actcc                                            25

SEQ ID NO: 12            moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 12
aatactgagc ggtgtccact ccgac                                            25

SEQ ID NO: 13            moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 13
agtaatactg agcggtgtcc actcc                                            25

SEQ ID NO: 14            moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 14
gaaagtaata ctgagcggtg tccac                                            25

SEQ ID NO: 15            moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 15
gcagaaagta atactgagcg gtgtc                                            25

SEQ ID NO: 16            moltype = DNA  length = 25
FEATURE                  Location/Qualifiers
```

```
misc_feature              1..25
                          note = Synthetic sequence
source                    1..25
                          mol_type = other DNA
                          organism = synthetic construct
SEQUENCE: 16
gcggcagaaa gtaatactga gcggt                                                          25

SEQ ID NO: 17             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 17
acagcggcag aaagtaatac tgagc                                                          25

SEQ ID NO: 18             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 18
ttgacagcgg cagaaagtaa tactg                                                          25

SEQ ID NO: 19             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 19
gccttgacag cggcagaaag taata                                                          25

SEQ ID NO: 20             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 20
tcggccttga cagcggcaga aagta                                                          25

SEQ ID NO: 21             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 21
ccctcggcct tgacagcggc agaaa                                                          25

SEQ ID NO: 22             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 22
tggccctcgg ccttgacagc ggcag                                                          25

SEQ ID NO: 23             moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 23
gcctggccct cggccttgac agcgg                                                          25

SEQ ID NO: 24             moltype = DNA   length = 25
```

-continued

```
FEATURE             Location/Qualifiers
misc_feature        1..25
                    note = Synthetic sequence
source              1..25
                    mol_type = other DNA
                    organism = synthetic construct
SEQUENCE: 24
tctgcctggc cctcggcctt gacag                                    25

SEQ ID NO: 25       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 25
cattctgcct ggccctcggc cttga                                    25

SEQ ID NO: 26       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 26
agccattctg cctggccctc ggcct                                    25

SEQ ID NO: 27       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 27
tgcagccatt ctgcctggcc ctcgg                                    25

SEQ ID NO: 28       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 28
acgtgcagcc attctgcctg gccct                                    25

SEQ ID NO: 29       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 29
cctacgtgca gccattctgc ctggc                                    25

SEQ ID NO: 30       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 30
gaacctacgt gcagccattc tgcct                                    25

SEQ ID NO: 31       moltype = DNA   length = 25
FEATURE             Location/Qualifiers
misc_feature        1..25
                    note = Synthetic sequence
source              1..25
                    mol_type = other DNA
                    organism = synthetic construct
SEQUENCE: 31
ggggaaccta cgtgcagcca ttctg                                    25
```

-continued

```
SEQ ID NO: 32            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 32
tctgggaac ctacgtgcag ccatt                                       25

SEQ ID NO: 33            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 33
ctctctgggg aacctacgtg cagcc                                      25

SEQ ID NO: 34            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 34
ctgctctctg gggaacctac gtgca                                      25

SEQ ID NO: 35            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 35
tgcctgctct ctggggaacc tacgt                                      25

SEQ ID NO: 36            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 36
ccctgcctgc tctctgggga accta                                      25

SEQ ID NO: 37            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 37
tgccctgcc tgctctctgg ggaac                                       25

SEQ ID NO: 38            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 38
agatgcccct gcctgctctc tgggg                                      25

SEQ ID NO: 39            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 39
gacagatgcc cctgcctgct ctctg                                      25
```

-continued

```
SEQ ID NO: 40           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 40
acagacagat gcccctgcct gctct                                        25

SEQ ID NO: 41           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 41
cagacagaca gatgcccctg cctgc                                        25

SEQ ID NO: 42           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 42
ccacagacag acagatgccc ctgcc                                        25

SEQ ID NO: 43           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 43
agcccacaga cagacagatg cccct                                        25

SEQ ID NO: 44           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 44
tgaagcccac agacagacag atgcc                                        25

SEQ ID NO: 45           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 45
tgctgaagcc cacagacaga cagat                                        25

SEQ ID NO: 46           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 46
aagtgctgaa gcccacagac agaca                                        25

SEQ ID NO: 47           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 47
```

```
ttaaagtgct gaagcccaca gacag                                    25

SEQ ID NO: 48          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 48
tctttaaagt gctgaagccc acaga                                    25

SEQ ID NO: 49          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 49
gcctctttaa agtgctgaag cccac                                    25

SEQ ID NO: 50          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 50
acagcctctt taaagtgctg aagcc                                    25

SEQ ID NO: 51          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 51
cacacagcct ctttaaagtg ctgaa                                    25

SEQ ID NO: 52          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 52
ggccacacag cctctttaaa gtgct                                    25

SEQ ID NO: 53          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 53
gttggccaca cagcctcttt aaagt                                    25

SEQ ID NO: 54          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 54
ctggttggcc acacagcctc tttaa                                    25

SEQ ID NO: 55          moltype = DNA   length = 25
FEATURE                Location/Qualifiers
misc_feature           1..25
                       note = Synthetic sequence
source                 1..25
                       mol_type = other DNA
                       organism = synthetic construct
```

```
SEQUENCE: 55
gtcctggttg gccacacagc ctctt                                                  25

SEQ ID NO: 56              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 56
tgggtcctgg ttggccacac agcct                                                  25

SEQ ID NO: 57              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 57
ccctgggtcc tggttggcca cacag                                                  25

SEQ ID NO: 58              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 58
ggaccctggg tcctggttgg ccaca                                                  25

SEQ ID NO: 59              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 59
aggggaccct gggtcctggt tggcc                                                  25

SEQ ID NO: 60              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 60
gggagggggac cctgggtcct ggttg                                                 25

SEQ ID NO: 61              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 61
ctggggaggg gaccctgggt cctgg                                                  25

SEQ ID NO: 62              moltype = DNA  length = 25
FEATURE                    Location/Qualifiers
misc_feature               1..25
                           note = Synthetic sequence
source                     1..25
                           mol_type = other DNA
                           organism = synthetic construct
SEQUENCE: 62
gagctgggga ggggaccctg ggtcc                                                  25

SEQ ID NO: 63              moltype = DNA  length = 25
FEATURE                    Location/Qualifiers
misc_feature               1..25
                           note = Synthetic sequence
source                     1..25
                           mol_type = other DNA
```

```
                           organism = synthetic construct
SEQUENCE: 63
agggagctgg ggaggggacc ctggg                                           25

SEQ ID NO: 64            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 64
ccaagggagc tggggagggg accct                                           25

SEQ ID NO: 65            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 65
ttcccaaggg agctggggag gggac                                           25

SEQ ID NO: 66            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 66
tccttcccaa gggagctggg gaggg                                           25

SEQ ID NO: 67            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 67
gtgtccttcc caagggagct gggga                                           25

SEQ ID NO: 68            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 68
gctgtgtcct tcccaaggga gctgg                                           25

SEQ ID NO: 69            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 69
actgctgtgt ccttcccaag ggagc                                           25

SEQ ID NO: 70            moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 70
aatactgctg tgtccttccc aaggg                                           25

SEQ ID NO: 71            moltype = DNA   length = 25
FEATURE                  Location/Qualifiers
misc_feature             1..25
                         note = Synthetic sequence
source                   1..25
```

-continued

```
                             mol_type = other DNA
                             organism = synthetic construct
SEQUENCE: 71
tccaatactg ctgtgtcctt cccaa                                            25

SEQ ID NO: 72          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 72
ccgtccaata ctgctgtgtc cttcc                                            25

SEQ ID NO: 73          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 73
aaaccgtcca atactgctgt gtcct                                            25

SEQ ID NO: 74          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 74
tagaaaccgt ccaatactgc tgtgt                                            25

SEQ ID NO: 75          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 75
ggctagaaac cgtccaatac tgctg                                            25

SEQ ID NO: 76          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 76
agaggctaga aaccgtccaa tactg                                            25

SEQ ID NO: 77          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 77
ctcagaggct agaaaccgtc caata                                            25

SEQ ID NO: 78          moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 78
catctcagag gctagaaacc gtcca                                            25

SEQ ID NO: 79          moltype = DNA   length = 25
FEATURE                Location/Qualifiers
misc_feature           1..25
                       note = Synthetic sequence
```

-continued

```
source                    1..25
                          mol_type = other DNA
                          organism = synthetic construct
SEQUENCE: 79
tagcatctca gaggctagaa accgt                                     25

SEQ ID NO: 80            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 80
aattagcatc tcagaggcta gaaac                                     25

SEQ ID NO: 81            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 81
ataaattagc atctcagagg ctaga                                     25

SEQ ID NO: 82            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 82
gaaataaatt agcatctcag aggct                                     25

SEQ ID NO: 83            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 83
ggggaaataa attagcatct cagag                                     25

SEQ ID NO: 84            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 84
ctcggggaaa taaattagca tctca                                     25

SEQ ID NO: 85            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 85
ggactcgggg aaataaatta gcatc                                     25

SEQ ID NO: 86            moltype = DNA   length = 25
FEATURE                  Location/Qualifiers
misc_feature             1..25
                          note = Synthetic sequence
source                    1..25
                          mol_type = other DNA
                          organism = synthetic construct
SEQUENCE: 86
tgaggactcg gggaaataaa ttagc                                     25

SEQ ID NO: 87            moltype = DNA   length = 25
FEATURE                  Location/Qualifiers
misc_feature             1..25
```

```
                              note = Synthetic sequence
source                        1..25
                              mol_type = other DNA
                              organism = synthetic construct
SEQUENCE: 87
acctgaggac tcgggggaaat aaatt                                              25

SEQ ID NO: 88                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 88
tgtacctgag gactcgggga aataa                                              25

SEQ ID NO: 89                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 89
cgctgtacct gaggactcgg ggaaa                                              25

SEQ ID NO: 90                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 90
gcccgctgta cctgaggact cgggg                                              25

SEQ ID NO: 91                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 91
acagcccgct gtacctgagg actcg                                              25

SEQ ID NO: 92                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 92
ggcacagccc gctgtacctg aggac                                              25

SEQ ID NO: 93                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 93
ccgggcacag cccgctgtac ctgag                                              25

SEQ ID NO: 94                 moltype = DNA   length = 25
FEATURE                       Location/Qualifiers
misc_feature                  1..25
                              note = Synthetic sequence
source                        1..25
                              mol_type = other DNA
                              organism = synthetic construct
SEQUENCE: 94
gggccgggca gcccgctg tacct                                                25

SEQ ID NO: 95                 moltype = DNA   length = 25
FEATURE                       Location/Qualifiers
```

```
misc_feature            1..25
                        note = Synthetic sequence
source                  1..25
                        mol_type = other DNA
                        organism = synthetic construct
SEQUENCE: 95
gtggggccgg gcacagcccg ctgta                                          25

SEQ ID NO: 96           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 96
ggggtggggc cgggcacagc ccgct                                          25

SEQ ID NO: 97           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 97
caggggtgg ggccgggcac agccc                                           25

SEQ ID NO: 98           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 98
gcccaggggg tggggccggg cacag                                          25

SEQ ID NO: 99           moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 99
tctgcccagg gggtggggcc gggca                                          25

SEQ ID NO: 100          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 100
acatctgccc aggggtggg gccgg                                           25

SEQ ID NO: 101          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 101
gggacatctg cccaggggggt ggggc                                         25

SEQ ID NO: 102          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 102
tgggggacat ctgcccaggg ggtgg                                          25

SEQ ID NO: 103          moltype = DNA   length = 25
```

-continued

```
FEATURE                Location/Qualifiers
misc_feature           1..25
                       note = Synthetic sequence
source                 1..25
                       mol_type = other DNA
                       organism = synthetic construct
SEQUENCE: 103
cagtgggggA catctgccca ggggg                                          25

SEQ ID NO: 104         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 104
tagcagtggg ggacatctgc ccagg                                          25

SEQ ID NO: 105         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 105
ccttagcagt gggggacatc tgccc                                          25

SEQ ID NO: 106         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 106
cagccttagc agtgggggac atctg                                          25

SEQ ID NO: 107         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 107
cagcagcctt agcagtgggg gacat                                          25

SEQ ID NO: 108         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 108
agccagcagc cttagcagtg gggga                                          25

SEQ ID NO: 109         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 109
tgaagccagc agccttagca gtggg                                          25

SEQ ID NO: 110         moltype = DNA   length = 25
FEATURE                Location/Qualifiers
misc_feature           1..25
                       note = Synthetic sequence
source                 1..25
                       mol_type = other DNA
                       organism = synthetic construct
SEQUENCE: 110
ccctgaagcc agcagcctta gcagt                                          25
```

-continued

```
SEQ ID NO: 111          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 111
cctccctgaa gccagcagcc ttagc                                         25

SEQ ID NO: 112          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 112
aaccctccct gaagccagca gcctt                                         25

SEQ ID NO: 113          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 113
gctaaccctc cctgaagcca gcagc                                         25

SEQ ID NO: 114          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 114
caggctaacc ctccctgaag ccagc                                         25

SEQ ID NO: 115          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 115
gtgcaggcta accctccctg aagcc                                         25

SEQ ID NO: 116          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 116
gcggtgcagg ctaaccctcc ctgaa                                         25

SEQ ID NO: 117          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 117
gcggcggtgc aggctaaccc tccct                                         25

SEQ ID NO: 118          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 118
gtggcggcgg tgcaggctaa ccctc                                         25
```

-continued

```
SEQ ID NO: 119          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 119
agggtggcgg cggtgcaggc taacc                                          25

SEQ ID NO: 120          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 120
ggcagggtgg cggcggtgca ggcta                                          25

SEQ ID NO: 121          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 121
aggggcaggg tggcggcggt gcagg                                          25

SEQ ID NO: 122          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 122
cttaggggca gggtggcggc ggtgc                                          25

SEQ ID NO: 123          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 123
taacttaggg gcagggtggc ggcgg                                          25

SEQ ID NO: 124          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 124
taataactta ggggcagggt ggcgg                                          25

SEQ ID NO: 125          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 125
aggtaataac ttaggggcag ggtgg                                          25

SEQ ID NO: 126          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 126
```

-continued

```
gagaggtaat aacttagggg caggg                                          25

SEQ ID NO: 127          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 127
ctggagaggt aataacttag gggca                                          25

SEQ ID NO: 128          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 128
gaactggaga ggtaataact taggg                                          25

SEQ ID NO: 129          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 129
taggaactgg agaggtaata actta                                          25

SEQ ID NO: 130          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 130
cggtaggaac tggagaggta ataac                                          25

SEQ ID NO: 131          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 131
gtacggtagg aactggagag gtaat                                          25

SEQ ID NO: 132          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 132
ggagtacggt aggaactgga gaggt                                          25

SEQ ID NO: 133          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 133
cagggagtac ggtaggaact ggaga                                          25

SEQ ID NO: 134          moltype = DNA   length = 25
FEATURE                 Location/Qualifiers
misc_feature            1..25
                        note = Synthetic sequence
source                  1..25
                        mol_type = other DNA
                        organism = synthetic construct
```

```
SEQUENCE: 134
gtgcagggag tacggtagga actgg                                          25

SEQ ID NO: 135          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 135
acggtgcagg gagtacggta ggaac                                          25

SEQ ID NO: 136          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 136
gagacggtgc agggagtacg gtagg                                          25

SEQ ID NO: 137          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 137
agtgagacgg tgcagggagt acggt                                          25

SEQ ID NO: 138          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 138
cacagtgaga cggtgcaggg agtac                                          25

SEQ ID NO: 139          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 139
acacacagtg agacggtgca gggag                                          25

SEQ ID NO: 140          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 140
gagacacaca gtgagacggt gcagg                                          25

SEQ ID NO: 141          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 141
cacgagacac acagtgagac ggtgc                                          25

SEQ ID NO: 142          moltype = DNA   length = 25
FEATURE                 Location/Qualifiers
misc_feature            1..25
                        note = Synthetic sequence
source                  1..25
                        mol_type = other DNA
```

```
                            organism = synthetic construct
SEQUENCE: 142
tgacacgaga cacacagtga gacgg                                         25

SEQ ID NO: 143          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 143
tactgacacg agacacacag tgaga                                         25

SEQ ID NO: 144          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 144
aattactgac acgagacaca cagtg                                         25

SEQ ID NO: 145          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 145
ataaattact gacacgagac acaca                                         25

SEQ ID NO: 146          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 146
catataaatt actgacacga gacac                                         25

SEQ ID NO: 147          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 147
caccatataa attactgaca cgaga                                         25

SEQ ID NO: 148          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 148
taacaccata taaattactg acacg                                         25

SEQ ID NO: 149          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 149
ttttaacacc atataaatta ctgac                                         25

SEQ ID NO: 150          moltype = DNA  length = 25
FEATURE                 Location/Qualifiers
misc_feature            1..25
                        note = Synthetic sequence
source                  1..25
```

```
                         mol_type = other DNA
                         organism = synthetic construct
SEQUENCE: 150
acattttaac accatataaa ttact                                              25

SEQ ID NO: 151          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 151
tacacatttt aacaccatat aaatt                                              25

SEQ ID NO: 152          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 152
atatacacat tttaacacca tataa                                              25

SEQ ID NO: 153          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 153
aaaatataca cattttaaca ccata                                              25

SEQ ID NO: 154          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 154
acaaaaatat acacatttta acacc                                              25

SEQ ID NO: 155          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 155
catacaaaaa tatacacatt ttaac                                              25

SEQ ID NO: 156          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 156
tgacatacaa aaatatacac atttt                                              25

SEQ ID NO: 157          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 157
tagtgacata caaaaatata cacat                                              25

SEQ ID NO: 158          moltype = DNA   length = 25
FEATURE                 Location/Qualifiers
misc_feature            1..25
                        note = Synthetic sequence
```

-continued

```
source                  1..25
                        mol_type = other DNA
                        organism = synthetic construct
SEQUENCE: 158
aaatagtgac atacaaaaat ataca                                              25

SEQ ID NO: 159          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 159
tgaaaatagt gacatacaaa aatat                                              25

SEQ ID NO: 160          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 160
tagtgaaaat agtgacatac aaaaa                                              25

SEQ ID NO: 161          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 161
ccctagtgaa aatagtgaca tacaa                                              25

SEQ ID NO: 162          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 162
cagccctagt gaaaatagtg acata                                              25

SEQ ID NO: 163          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 163
cctcagccct agtgaaaata gtgac                                              25

SEQ ID NO: 164          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 164
gccctcagc cctagtgaaa atagt                                               25

SEQ ID NO: 165          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 165
caggcccctc agccctagtg aaaat                                              25

SEQ ID NO: 166          moltype = DNA   length = 25
FEATURE                 Location/Qualifiers
misc_feature            1..25
```

-continued

```
                         note = Synthetic sequence
source                   1..25
                         mol_type = other DNA
                         organism = synthetic construct
SEQUENCE: 166
gcgcaggccc ctcagccta gtgaa                                      25

SEQ ID NO: 167           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 167
tgggcgcagg ccctcagcc ctagt                                      25

SEQ ID NO: 168           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 168
ctctgggcgc aggcccctca gccct                                     25

SEQ ID NO: 169           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 169
cagctctggg cgcaggcccc tcagc                                     25

SEQ ID NO: 170           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 170
ggccagctct gggcgcaggc ccctc                                     25

SEQ ID NO: 171           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 171
ggaggccagc tctgggcgca ggccc                                     25

SEQ ID NO: 172           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 172
ggggggaggcc agctctgggc gcagg                                    25

SEQ ID NO: 173           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 173
gttgggggag gccagctctg ggcgc                                     25

SEQ ID NO: 174           moltype = DNA  length = 25
FEATURE                  Location/Qualifiers
```

```
misc_feature              1..25
                          note = Synthetic sequence
source                    1..25
                          mol_type = other DNA
                          organism = synthetic construct
SEQUENCE: 174
ggtgttgggg gaggccagct ctggg                                               25

SEQ ID NO: 175            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 175
gcaggtgttg gggaggcca gctct                                                25

SEQ ID NO: 176            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 176
gcagcaggtg ttgggggagg ccagc                                               25

SEQ ID NO: 177            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 177
agcgcagcag gtgttggggg aggcc                                               25

SEQ ID NO: 178            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 178
ccaagcgcag caggtgttgg gggag                                               25

SEQ ID NO: 179            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 179
ctaccaagcg cagcaggtgt tgggg                                               25

SEQ ID NO: 180            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 180
cacctaccaa gcgcagcagg tgttg                                               25

SEQ ID NO: 181            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 181
ccacacctac caagcgcagc aggtg                                               25

SEQ ID NO: 182            moltype = DNA   length = 25
```

-continued

```
FEATURE               Location/Qualifiers
misc_feature          1..25
                      note = Synthetic sequence
source                1..25
                      mol_type = other DNA
                      organism = synthetic construct
SEQUENCE: 182
ccaccacacc taccaagcgc agcag                                        25

SEQ ID NO: 183        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 183
acgccaccac acctaccaag cgcag                                        25

SEQ ID NO: 184        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 184
ataacgccac cacacctacc aagcg                                        25

SEQ ID NO: 185        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 185
gccataacgc caccacacct accaa                                        25

SEQ ID NO: 186        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 186
gctgccataa cgccaccaca cctac                                        25

SEQ ID NO: 187        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 187
cgggctgcca taacgccacc acacc                                        25

SEQ ID NO: 188        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 188
agccgggctg ccataacgcc accac                                        25

SEQ ID NO: 189        moltype = DNA   length = 25
FEATURE               Location/Qualifiers
misc_feature          1..25
                      note = Synthetic sequence
source                1..25
                      mol_type = other DNA
                      organism = synthetic construct
SEQUENCE: 189
agcagccggg ctgccataac gccac                                        25
```

-continued

```
SEQ ID NO: 190          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 190
agcagcagcc gggctgccat aacgc                                   25

SEQ ID NO: 191          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 191
ccaagcagca gccgggctgc cataa                                   25

SEQ ID NO: 192          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 192
catccaagca gcagccgggc tgcca                                   25

SEQ ID NO: 193          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 193
tcgcatccaa gcagcagccg ggctg                                   25

SEQ ID NO: 194          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 194
agctcgcatc caagcagcag ccggg                                   25

SEQ ID NO: 195          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 195
ccaagctcgc atccaagcag cagcc                                   25

SEQ ID NO: 196          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 196
aggccaagct cgcatccaag cagca                                   25

SEQ ID NO: 197          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 197
ccaaggccaa gctcgcatcc aagca                                   25
```

-continued

```
SEQ ID NO: 198          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 198
ggcccaaggc caagctcgca tccaa                                       25

SEQ ID NO: 199          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 199
accggcccaa ggccaagctc gcatc                                       25

SEQ ID NO: 200          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 200
agcaccggcc caaggccaag ctcgc                                       25

SEQ ID NO: 201          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 201
cccagcaccg gcccaaggcc aagct                                       25

SEQ ID NO: 202          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 202
gcccccagca ccggcccaag gccaa                                       25

SEQ ID NO: 203          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 203
tgtgcccca gcaccggccc aaggc                                        25

SEQ ID NO: 204          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 204
agctgtgccc ccagcaccgg cccaa                                       25

SEQ ID NO: 205          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 205
```

-continued

```
gacagctgtg cccccagcac cggcc                                              25

SEQ ID NO: 206          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 206
gcagacagct gtgcccccag caccg                                              25

SEQ ID NO: 207          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 207
ctggcagaca gctgtgcccc cagca                                              25

SEQ ID NO: 208          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 208
tgcctggcag acagctgtgc cccca                                              25

SEQ ID NO: 209          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 209
gagtgcctgg cagacagctg tgccc                                              25

SEQ ID NO: 210          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 210
tgagagtgcc tggcagacag ctgtg                                              25

SEQ ID NO: 211          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 211
tgatgagagt gcctggcaga cagct                                              25

SEQ ID NO: 212          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 212
gggtgatgag agtgcctggc agaca                                              25

SEQ ID NO: 213          moltype = DNA   length = 25
FEATURE                 Location/Qualifiers
misc_feature            1..25
                        note = Synthetic sequence
source                  1..25
                        mol_type = other DNA
                        organism = synthetic construct
```

```
SEQUENCE: 213
ctggggtgat gagagtgcct ggcag                                                     25

SEQ ID NO: 214          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 214
cctctggggt gatgagagtg cctgg                                                     25

SEQ ID NO: 215          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 215
aggcctctgg ggtgatgaga gtgcc                                                     25

SEQ ID NO: 216          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 216
acaaggcctc tggggtgatg agagt                                                     25

SEQ ID NO: 217          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 217
atgacaaggc ctctggggtg atgag                                                     25

SEQ ID NO: 218          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 218
aggatgacaa ggcctctggg gtgat                                                     25

SEQ ID NO: 219          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 219
gggaggatga caaggcctct ggggt                                                     25

SEQ ID NO: 220          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 220
caagggagga tgacaaggcc tctgg                                                     25

SEQ ID NO: 221          moltype = DNA  length = 25
FEATURE                 Location/Qualifiers
misc_feature            1..25
                        note = Synthetic sequence
source                  1..25
                        mol_type = other DNA
```

```
                          organism = synthetic construct
SEQUENCE: 221
gggcaaggga ggatgacaag gcctc                                          25

SEQ ID NO: 222           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 222
ctggggcaag ggaggatgac aaggc                                          25

SEQ ID NO: 223           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 223
ggcctggggc aagggaggat gacaa                                          25

SEQ ID NO: 224           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 224
cctggcctgg ggcaagggag gatga                                          25

SEQ ID NO: 225           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 225
ctacctggcc tggggcaagg gagga                                          25

SEQ ID NO: 226           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 226
ttgctacctg gcctggggca aggga                                          25

SEQ ID NO: 227           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 227
ctcttgctac ctggcctggg gcaag                                          25

SEQ ID NO: 228           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 228
gctctcttgc tacctggcct ggggc                                          25

SEQ ID NO: 229           moltype = DNA   length = 25
FEATURE                  Location/Qualifiers
misc_feature             1..25
                         note = Synthetic sequence
source                   1..25
```

```
                              mol_type = other DNA
                              organism = synthetic construct
SEQUENCE: 229
gctgctctct tgctacctgg cctgg                                          25

SEQ ID NO: 230           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 230
ggcgctgctc tcttgctacc tggcc                                          25

SEQ ID NO: 231           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 231
ctgggcgctg ctctcttgct acctg                                          25

SEQ ID NO: 232           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 232
ggcctgggcg ctgctctctt gctac                                          25

SEQ ID NO: 233           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 233
gcaggcctgg gcgctgctct cttgc                                          25

SEQ ID NO: 234           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 234
ccagcaggcc tgggcgctgc tctct                                          25

SEQ ID NO: 235           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 235
atgccagcag gcctgggcgc tgctc                                          25

SEQ ID NO: 236           moltype = DNA   length = 25
FEATURE                  Location/Qualifiers
misc_feature             1..25
                         note = Synthetic sequence
source                   1..25
                         mol_type = other DNA
                         organism = synthetic construct
SEQUENCE: 236
ctgatgccag caggcctggg cgctg                                          25

SEQ ID NO: 237           moltype = DNA   length = 25
FEATURE                  Location/Qualifiers
misc_feature             1..25
                         note = Synthetic sequence
```

-continued

```
source                    1..25
                          mol_type = other DNA
                          organism = synthetic construct
SEQUENCE: 237
gacctgatgc cagcaggcct gggcg                                      25

SEQ ID NO: 238            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 238
ccagacctga tgccagcagg cctgg                                      25

SEQ ID NO: 239            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 239
tgcccagacc tgatgccagc aggcc                                      25

SEQ ID NO: 240            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 240
acttgcccag acctgatgcc agcag                                      25

SEQ ID NO: 241            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 241
gctacttgcc cagacctgat gccag                                      25

SEQ ID NO: 242            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 242
cctgctactt gcccagacct gatgc                                      25

SEQ ID NO: 243            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 243
agtcctgcta cttgcccaga cctga                                      25

SEQ ID NO: 244            moltype = DNA   length = 25
FEATURE                   Location/Qualifiers
misc_feature              1..25
                          note = Synthetic sequence
source                    1..25
                          mol_type = other DNA
                          organism = synthetic construct
SEQUENCE: 244
cctagtcctg ctacttgccc agacc                                      25

SEQ ID NO: 245            moltype = DNA   length = 25
FEATURE                   Location/Qualifiers
misc_feature              1..25
```

-continued

```
                         note = Synthetic sequence
source                   1..25
                         mol_type = other DNA
                         organism = synthetic construct
SEQUENCE: 245
atgcctagtc ctgctacttg cccag                                      25

SEQ ID NO: 246           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 246
gacatgccta gtcctgctac ttgcc                                      25

SEQ ID NO: 247           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 247
tctgacatgc ctagtcctgc tactt                                      25

SEQ ID NO: 248           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 248
tcctctgaca tgcctagtcc tgcta                                      25

SEQ ID NO: 249           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 249
gggtcctctg acatgcctag tcctg                                      25

SEQ ID NO: 250           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 250
ctggggtcct ctgacatgcc tagtc                                      25

SEQ ID NO: 251           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 251
accctggggt cctctgacat gccta                                      25

SEQ ID NO: 252           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 252
accaccctgg ggtcctctga catgc                                      25

SEQ ID NO: 253           moltype = DNA  length = 25
FEATURE                  Location/Qualifiers
```

-continued

```
misc_feature            1..25
                        note = Synthetic sequence
source                  1..25
                        mol_type = other DNA
                        organism = synthetic construct
SEQUENCE: 253
ctaaccaccc tggggtcctc tgaca                                         25

SEQ ID NO: 254          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 254
cctctaacca ccctggggtc ctctg                                         25

SEQ ID NO: 255          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 255
tttcctctaa ccaccctggg gtcct                                         25

SEQ ID NO: 256          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 256
tcttttcctc taaccaccct ggggt                                         25

SEQ ID NO: 257          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 257
gagtcttttc tctaaccac cctgg                                          25

SEQ ID NO: 258          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 258
gaggagtctt ttcctctaac caccc                                         25

SEQ ID NO: 259          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 259
caggaggagt cttttcctct aacca                                         25

SEQ ID NO: 260          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 260
ccccaggagg agtcttttcc tctaa                                         25

SEQ ID NO: 261          moltype = DNA   length = 25
```

-continued

```
FEATURE              Location/Qualifiers
misc_feature         1..25
                     note = Synthetic sequence
source               1..25
                     mol_type = other DNA
                     organism = synthetic construct
SEQUENCE: 261
agccccagg aggagtcttt tcctc                                  25

SEQ ID NO: 262       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 262
gccagccccc aggaggagtc ttttc                                 25

SEQ ID NO: 263       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 263
ggagccagcc cccaggagga gtctt                                 25

SEQ ID NO: 264       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 264
ctgggagcca gcccccagga ggagt                                 25

SEQ ID NO: 265       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 265
accctgggag ccagccccca ggagg                                 25

SEQ ID NO: 266       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 266
tccaccctgg gagccagccc ccagg                                 25

SEQ ID NO: 267       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 267
tcctccaccc tgggagccag ccccc                                 25

SEQ ID NO: 268       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 268
ccttcctcca ccctgggagc cagcc                                 25
```

-continued

```
SEQ ID NO: 269          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 269
tcaccttcct ccaccctggg agcca                                        25

SEQ ID NO: 270          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 270
cagtcacctt cctccaccct gggag                                        25

SEQ ID NO: 271          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 271
acacagtcac cttcctccac cctgg                                        25

SEQ ID NO: 272          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 272
cacacacagt caccttcctc caccc                                        25

SEQ ID NO: 273          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 273
acacacacac agtcaccttc ctcca                                        25

SEQ ID NO: 274          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 274
cacacacaca cacagtcacc ttcct                                        25

SEQ ID NO: 275          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 275
acacacacac acacagtc acctt                                          25

SEQ ID NO: 276          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 276
cgcacacaca cacacacaca gtcac                                        25
```

```
SEQ ID NO: 277          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 277
gcgcgcacac acacacacac acagt                                          25

SEQ ID NO: 278          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 278
cgcgcgcgca cacacacaca cacac                                          25

SEQ ID NO: 279          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 279
gtgcgcgcgc gcacacacac acaca                                          25

SEQ ID NO: 280          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 280
cgcgtgcgcg cgcgcacaca cacac                                          25

SEQ ID NO: 281          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 281
tcgcgcgtgc gcgcgcgcac acaca                                          25

SEQ ID NO: 282          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 282
cactcgcgcg tgcgcgcgcg cacac                                          25

SEQ ID NO: 283          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 283
gcacactcgc gcgtgcgcgc gcgca                                          25

SEQ ID NO: 284          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 284
```

-continued

```
acagcacact cgcgcgtgcg cgcgc                                        25

SEQ ID NO: 285          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 285
catacagcac actcgcgcgt gcgcg                                        25

SEQ ID NO: 286          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 286
ggccatacag cacactcgcg cgtgc                                        25

SEQ ID NO: 287          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 287
ctgggccata cagcacactc gcgcg                                        25

SEQ ID NO: 288          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 288
tgcctgggcc atacagcaca ctcgc                                        25

SEQ ID NO: 289          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 289
ggctgcctgg gccatacagc acact                                        25

SEQ ID NO: 290          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 290
tgaggctgcc tgggccatac agcac                                        25

SEQ ID NO: 291          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 291
ccttgaggct gcctgggcca tacag                                        25

SEQ ID NO: 292          moltype = DNA   length = 25
FEATURE                 Location/Qualifiers
misc_feature            1..25
                        note = Synthetic sequence
source                  1..25
                        mol_type = other DNA
                        organism = synthetic construct
```

-continued

```
SEQUENCE: 292
gggccttgag gctgcctggg ccata                                              25

SEQ ID NO: 293          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 293
cgagggcctt gaggctgcct gggcc                                              25

SEQ ID NO: 294          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 294
ctccgagggc cttgaggctg cctgg                                              25

SEQ ID NO: 295          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 295
cagctccgag ggccttgagg ctgcc                                              25

SEQ ID NO: 296          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 296
agccagctcc gagggccttg aggct                                              25

SEQ ID NO: 297          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 297
cacagccagc tccgagggcc ttgag                                              25

SEQ ID NO: 298          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 298
aggcacagcc agctccgagg gcctt                                              25

SEQ ID NO: 299          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 299
agcaggcaca gccagctccg agggc                                              25

SEQ ID NO: 300          moltype = DNA   length = 25
FEATURE                 Location/Qualifiers
misc_feature            1..25
                        note = Synthetic sequence
source                  1..25
                        mol_type = other DNA
```

-continued

```
                              organism = synthetic construct
SEQUENCE: 300
agaagcaggc acagccagct ccgag                                         25

SEQ ID NO: 301         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 301
cacagaagca ggcacagcca gctcc                                         25

SEQ ID NO: 302         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 302
gtacacagaa gcaggcacag ccagc                                         25

SEQ ID NO: 303         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 303
gtggtacaca gaagcaggca cagcc                                         25

SEQ ID NO: 304         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 304
gaagtggtac acagaagcag gcaca                                         25

SEQ ID NO: 305         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 305
acagaagtgg tacacagaag caggc                                         25

SEQ ID NO: 306         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 306
cccacagaag tggtacacag aagca                                         25

SEQ ID NO: 307         moltype = DNA  length = 25
FEATURE                Location/Qualifiers
misc_feature           1..25
                       note = Synthetic sequence
source                 1..25
                       mol_type = other DNA
                       organism = synthetic construct
SEQUENCE: 307
atgcccacag aagtggtaca cagaa                                         25

SEQ ID NO: 308         moltype = DNA  length = 25
FEATURE                Location/Qualifiers
misc_feature           1..25
                       note = Synthetic sequence
source                 1..25
```

-continued

```
                              mol_type = other DNA
                              organism = synthetic construct
SEQUENCE: 308
gccatgccca cagaagtggt acaca                                    25

SEQ ID NO: 309          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 309
gcggccatgc ccacagaagt ggtac                                    25

SEQ ID NO: 310          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 310
gaagcggcca tgcccacaga agtgg                                    25

SEQ ID NO: 311          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 311
ctagaagcgg ccatgcccac agaag                                    25

SEQ ID NO: 312          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 312
gctctagaag cggccatgcc cacag                                    25

SEQ ID NO: 313          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 313
gaggctctag aagcggccat gccca                                    25

SEQ ID NO: 314          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 314
gtcgaggctc tagaagcggc catgc                                    25

SEQ ID NO: 315          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 315
ggtgtcgagg ctctagaagc ggcca                                    25

SEQ ID NO: 316          moltype = DNA  length = 25
FEATURE                 Location/Qualifiers
misc_feature            1..25
                        note = Synthetic sequence
```

-continued

```
source                   1..25
                         mol_type = other DNA
                         organism = synthetic construct
SEQUENCE: 316
gggggtgtcg aggctctaga agcgg                                        25

SEQ ID NO: 317           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 317
tggggggtg tcgaggctct agaag                                         25

SEQ ID NO: 318           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 318
ggttggggg gtgtcgaggc tctag                                         25

SEQ ID NO: 319           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 319
gggggttggg ggggtgtcga ggctc                                        25

SEQ ID NO: 320           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 320
tgcggggggtt ggggggtgt cgagg                                        25

SEQ ID NO: 321           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 321
tggtgcgggg gttgggggggg tgtcg                                       25

SEQ ID NO: 322           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 322
gcttggtgcg ggggttgggg gggtg                                        25

SEQ ID NO: 323           moltype = DNA  length = 25
FEATURE                  Location/Qualifiers
misc_feature             1..25
                         note = Synthetic sequence
source                   1..25
                         mol_type = other DNA
                         organism = synthetic construct
SEQUENCE: 323
tctgcttggt gcgggggttg ggggg                                        25

SEQ ID NO: 324           moltype = DNA  length = 25
FEATURE                  Location/Qualifiers
misc_feature             1..25
```

-continued

```
                          note = Synthetic sequence
source                    1..25
                          mol_type = other DNA
                          organism = synthetic construct
SEQUENCE: 324
ttgtctgctt ggtgcggggg ttggg                                      25

SEQ ID NO: 325            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 325
actttgtctg cttggtgcgg gggtt                                      25

SEQ ID NO: 326            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 326
ttgactttgt ctgcttggtg cgggg                                      25

SEQ ID NO: 327            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 327
ttattgactt tgtctgcttg gtgcg                                      25

SEQ ID NO: 328            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 328
cttttattga ctttgtctgc ttggt                                      25

SEQ ID NO: 329            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 329
gctcttttat tgactttgtc tgctt                                      25

SEQ ID NO: 330            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 330
acagctcttt tattgacttt gtctg                                      25

SEQ ID NO: 331            moltype = DNA  length = 25
FEATURE                   Location/Qualifiers
misc_feature              1..25
                          note = Synthetic sequence
source                    1..25
                          mol_type = other DNA
                          organism = synthetic construct
SEQUENCE: 331
cagacagctc ttttattgac tttgt                                      25

SEQ ID NO: 332            moltype = DNA  length = 25
FEATURE                   Location/Qualifiers
```

-continued

```
misc_feature          1..25
                      note = Synthetic sequence
source                1..25
                      mol_type = other DNA
                      organism = synthetic construct
SEQUENCE: 332
agtcagacag ctcttttatt gactt                                          25

SEQ ID NO: 333        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 333
tgcagtcaga cagctctttt attga                                          25

SEQ ID NO: 334        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 334
agcctcttta aagtgctgaa gccca                                          25

SEQ ID NO: 335        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 335
acacagcctc tttaaagtgc tgaag                                          25

SEQ ID NO: 336        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 336
gtccaatact gctgtgtcct ccca                                           25

SEQ ID NO: 337        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 337
gacagcggca gaaagtaata ctgag                                          25

SEQ ID NO: 338        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 338
ctctttaaag tgctgaagcc cacag                                          25

SEQ ID NO: 339        moltype = DNA  length = 25
FEATURE               Location/Qualifiers
misc_feature          1..25
                      note = Synthetic sequence
source                1..25
                      mol_type = other DNA
                      organism = synthetic construct
SEQUENCE: 339
cagcctcttt aaagtgctga agccc                                          25

SEQ ID NO: 340        moltype = DNA  length = 25
```

-continued

```
FEATURE              Location/Qualifiers
misc_feature         1..25
                     note = Synthetic sequence
source               1..25
                     mol_type = other DNA
                     organism = synthetic construct
SEQUENCE: 340
cacagcctct ttaaagtgct gaagc                                        25

SEQ ID NO: 341       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 341
ttaaagtgct gaagcccaca tacag                                        25

SEQ ID NO: 342       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 342
tctttaaagt gctgaagccc acata                                        25

SEQ ID NO: 343       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 343
ctctttaaag tgctgaagca cacag                                        25

SEQ ID NO: 344       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 344
gcctccttaa agtgctgaag cccac                                        25

SEQ ID NO: 345       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 345
agcctctata aagtgctgaa gccca                                        25

SEQ ID NO: 346       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 346
cagcctctat aaagtgctga agccc                                        25

SEQ ID NO: 347       moltype = DNA  length = 25
FEATURE              Location/Qualifiers
misc_feature         1..25
                     note = Synthetic sequence
source               1..25
                     mol_type = other DNA
                     organism = synthetic construct
SEQUENCE: 347
acagcctctt taaagtgctg aatcc                                        25
```

-continued

```
SEQ ID NO: 348          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 348
cacagcctct ttaaagtgct gaatc                                     25

SEQ ID NO: 349          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 349
acacaacctc tttaaagtgc tgaag                                     25

SEQ ID NO: 350          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 350
cacatagcct ctttaaagtg ctgaa                                     25

SEQ ID NO: 351          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 351
ggccacacag tctctttaaa gtgct                                     25

SEQ ID NO: 352          moltype = AA   length = 22
FEATURE                 Location/Qualifiers
REGION                  1..22
                        note = Synthetic sequence
source                  1..22
                        mol_type = protein
                        organism = synthetic construct
SEQUENCE: 352
RRSRTARAGR PGRNSSRPSA PR                                        22

SEQ ID NO: 353          moltype = DNA   length = 19
FEATURE                 Location/Qualifiers
misc_feature            1..19
                        note = Synthetic sequence
source                  1..19
                        mol_type = other DNA
                        organism = synthetic construct
SEQUENCE: 353
ttaaagtgct gaagcccac                                            19

SEQ ID NO: 354          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 354
ttaaagtgct gaagcccaca g                                         21

SEQ ID NO: 355          moltype = DNA   length = 23
FEATURE                 Location/Qualifiers
misc_feature            1..23
                        note = Synthetic sequence
source                  1..23
                        mol_type = other DNA
                        organism = synthetic construct
SEQUENCE: 355
ttaaagtgct gaagcccaca gac                                       23
```

-continued

```
SEQ ID NO: 356          moltype = DNA  length = 23
FEATURE                 Location/Qualifiers
misc_feature            1..23
                        note = Synthetic sequence
source                  1..23
                        mol_type = other DNA
                        organism = synthetic construct
SEQUENCE: 356
ttaaagtgct gaagctcaca gac                                        23

SEQ ID NO: 357          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 357
ttaaagtgct gaagctcaca gacag                                      25

SEQ ID NO: 358          moltype = DNA  length = 20
FEATURE                 Location/Qualifiers
misc_feature            1..20
                        note = Synthetic sequence
source                  1..20
                        mol_type = other DNA
                        organism = synthetic construct
SEQUENCE: 358
ttaaagtgct gaagcccaca                                            20

SEQ ID NO: 359          moltype = DNA  length = 22
FEATURE                 Location/Qualifiers
misc_feature            1..22
                        note = Synthetic sequence
source                  1..22
                        mol_type = other DNA
                        organism = synthetic construct
SEQUENCE: 359
ttaaagtgct gaagcccaca ga                                         22

SEQ ID NO: 360          moltype = DNA  length = 24
FEATURE                 Location/Qualifiers
misc_feature            1..24
                        note = Synthetic sequence
source                  1..24
                        mol_type = other DNA
                        organism = synthetic construct
SEQUENCE: 360
ttaaagtgct gaagcccaca gaca                                       24

SEQ ID NO: 361          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 361
ttaaagtact gaagcccaca gacag                                      25

SEQ ID NO: 362          moltype = DNA  length = 24
FEATURE                 Location/Qualifiers
misc_feature            1..24
                        note = Synthetic sequence
source                  1..24
                        mol_type = other DNA
                        organism = synthetic construct
SEQUENCE: 362
gtgctgaagc ccacagacag acag                                       24
```